US012036353B2

(12) United States Patent
Lin

(10) Patent No.: US 12,036,353 B2
(45) Date of Patent: Jul. 16, 2024

(54) APPARATUS AND METHODS FOR PRESSURE MANAGEMENT WITHIN A WOUND CHAMBER

(71) Applicant: Edward D. Lin, Osprey, FL (US)

(72) Inventor: Edward D. Lin, Osprey, FL (US)

(*) Notice: Subject to any disclaimer, the term of this patent is extended or adjusted under 35 U.S.C. 154(b) by 969 days.

(21) Appl. No.: 17/026,822

(22) Filed: Sep. 21, 2020

(65) Prior Publication Data

US 2021/0001022 A1 Jan. 7, 2021

Related U.S. Application Data

(63) Continuation-in-part of application No. 15/663,709, filed on Jul. 29, 2017, now abandoned, and a continuation-in-part of application No. 15/663,710, filed on Jul. 29, 2017, now Pat. No. 10,780,201.

(51) Int. Cl.
*A61M 1/00* (2006.01)

(52) U.S. Cl.
CPC .............. *A61M 1/912* (2021.05); *A61M 1/96* (2021.05); *A61M 1/92* (2021.05); *A61M 1/94* (2021.05); *A61M 2205/3331* (2013.01); *A61M 2205/6036* (2013.01)

(58) Field of Classification Search
CPC ............ A61F 13/00068; A61F 13/0216; A61F 13/0084; A61M 1/92; A61M 1/96
See application file for complete search history.

(56) References Cited

U.S. PATENT DOCUMENTS

| | | |
|---|---|---|
| 2,280,915 A | 4/1942 | Johnson |
| 3,026,874 A | 3/1962 | Stevens |
| 3,300,786 A | 1/1967 | Rosenvold et al. |
| 4,163,822 A | 8/1979 | Walter |
| 4,328,799 A | 5/1982 | LoPiano |
| 4,399,816 A | 8/1983 | Spangler |
| 4,635,618 A | 1/1987 | Munz |

(Continued)

FOREIGN PATENT DOCUMENTS

| | | |
|---|---|---|
| CH | 2010101399472 | 1/2016 |
| CN | 102008373 A | 4/2011 |

(Continued)

OTHER PUBLICATIONS

US 10,688,227, 07/2017, Lin (withdrawn)

(Continued)

*Primary Examiner* — Laura A Bouchelle
(74) *Attorney, Agent, or Firm* — James A Cardle

(57) ABSTRACT

A wound therapy apparatus disclosed herein includes a wound interface sealingly securable to a skin surface around a wound bed to form an enclosed space over the wound bed. An inflow fluid pathway and an outflow fluid pathway communicate fluidly with the enclosed space through an inflow port and an outflow port, respectively. The inflow port and the outflow port may be in spaced relation to define a flow path within the enclosed space equivalent in length to a characteristic length of the enclosed space. Pressure sensors may be in communication with the inflow fluid pathway and the outflow fluid pathway to detect inflow pressure $p_{in}$, and outflow pressure $p_{out}$.

20 Claims, 8 Drawing Sheets

(56) References Cited

U.S. PATENT DOCUMENTS

| | | |
|---|---|---|
| 5,086,763 A | 2/1992 | Hathman |
| 5,154,697 A | 10/1992 | Loori |
| D364,679 S | 11/1995 | Heaton et al. |
| 5,522,794 A | 6/1996 | Ewall |
| 5,562,107 A | 10/1996 | Lavender et al. |
| 5,607,388 A | 3/1997 | Ewall |
| 5,636,643 A | 6/1997 | Argenta et al. |
| 5,667,502 A | 9/1997 | Holtermann |
| 5,769,806 A | 6/1998 | Radow |
| 5,792,090 A | 8/1998 | Ladin |
| 5,899,207 A | 5/1999 | Scheinberg |
| 5,980,497 A | 11/1999 | Yavitz |
| 6,062,215 A | 5/2000 | Leininger et al. |
| 6,098,628 A | 8/2000 | Funk |
| 6,142,982 A | 11/2000 | Hunt et al. |
| 6,222,090 B1 | 4/2001 | Weston |
| 6,328,709 B1 | 12/2001 | Hung et al. |
| 6,458,109 B1 | 10/2002 | Henley et al. |
| 6,484,716 B1 | 11/2002 | Leininger et al. |
| D469,175 S | 1/2003 | Hall et al. |
| 6,553,998 B2 | 4/2003 | Heaton et al. |
| D475,134 S | 5/2003 | Randolph |
| 6,695,823 B1 | 2/2004 | Lina et al. |
| D488,588 S | 4/2004 | Murphy |
| 6,764,462 B2 | 7/2004 | Risk, Jr. et al. |
| 6,767,334 B1 | 7/2004 | Randolph |
| 6,767,344 B2 | 7/2004 | Suzuki |
| 6,814,079 B2 | 11/2004 | Heaton et al. |
| 6,824,533 B2 | 11/2004 | Risk, Jr. et al. |
| 6,856,821 B2 | 2/2005 | Johnson |
| 6,936,037 B2 | 8/2005 | Bubb et al. |
| 6,951,553 B2 | 10/2005 | Bubb et al. |
| 7,108,683 B2 | 9/2006 | Zamierowski |
| 7,154,017 B2 | 12/2006 | Sigurjonsson et al. |
| 7,520,866 B2 | 4/2009 | Stenzler et al. |
| 7,532,953 B2 | 5/2009 | Vogel |
| 7,534,240 B1 | 5/2009 | Johnson |
| 7,608,066 B2 | 10/2009 | Vogel |
| 7,790,945 B1 | 9/2010 | Watson, Jr. |
| 7,837,673 B2 | 11/2010 | Vogel |
| 7,909,805 B2 | 3/2011 | Weston |
| 7,964,766 B2 | 6/2011 | Blott et al. |
| D642,594 S | 8/2011 | Mattson et al. |
| D648,353 S | 11/2011 | Mattson et al. |
| 8,080,702 B2 | 12/2011 | Blott et al. |
| 8,142,405 B2 | 3/2012 | Vogel |
| 8,187,237 B2 | 5/2012 | Seegert |
| 8,529,532 B2 | 9/2013 | Pinto et al. |
| 8,529,548 B2 | 9/2013 | Blott et al. |
| 8,563,604 B2 | 10/2013 | Palefsky et al. |
| 8,708,982 B2 | 4/2014 | Lin |
| 8,821,419 B1 | 9/2014 | Beek |
| 9,782,512 B2 | 10/2017 | Blücher et al. |
| 9,907,940 B2 * | 3/2018 | Pratt ................ A61M 3/022 |
| 9,913,757 B2 | 3/2018 | Vitaris |
| 9,925,361 B2 | 3/2018 | Lin |
| 10,729,826 B2 | 8/2020 | Lin |
| 10,780,201 B2 | 9/2020 | Lin |
| 2001/0029956 A1 | 10/2001 | Argenta et al. |
| 2001/0041188 A1 | 11/2001 | Gibbins et al. |
| 2002/0017304 A1 | 2/2002 | Heaton et al. |
| 2002/0143286 A1 | 10/2002 | Tumey |
| 2002/0155164 A1 | 10/2002 | Figley et al. |
| 2003/0014022 A1 | 1/2003 | Lockwood et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0212357 A1 | 11/2003 | Pace |
| 2003/0219469 A1 | 11/2003 | Johnson et al. |
| 2004/0006319 A1 | 1/2004 | Lina et al. |
| 2004/0010207 A1 | 1/2004 | Flaherty et al. |
| 2004/0030304 A1 | 2/2004 | Hunt et al. |
| 2004/0073151 A1 | 4/2004 | Weston |
| 2004/0093026 A1 | 5/2004 | Weidenhagen et al. |
| 2004/0153032 A1 | 8/2004 | Garribotto et al. |
| 2004/0170703 A1 | 9/2004 | Hoekstra et al. |
| 2005/0137521 A1 | 6/2005 | Stenzler |
| 2005/0220849 A1 | 10/2005 | Hickey |
| 2005/0228340 A1 | 10/2005 | Cleary et al. |
| 2006/0127462 A1 | 6/2006 | Canada et al. |
| 2006/0146234 A1 | 7/2006 | Bear et al. |
| 2006/0185670 A1 | 8/2006 | Loori et al. |
| 2007/0041960 A1 | 2/2007 | Freeman et al. |
| 2007/0118096 A1 | 5/2007 | Smith et al. |
| 2007/0265586 A1 | 11/2007 | Joshi et al. |
| 2008/0140029 A1 | 6/2008 | Smith et al. |
| 2009/0258058 A1 | 10/2009 | Thomas et al. |
| 2009/0312723 A1 | 12/2009 | Blott et al. |
| 2010/0069858 A1 | 3/2010 | Olson |
| 2010/0268128 A1 | 10/2010 | Randolph |
| 2010/0298792 A1 | 11/2010 | Weston et al. |
| 2011/0160686 A1 | 6/2011 | Ueda et al. |
| 2012/0029449 A1 | 2/2012 | Khosrowshahi |
| 2012/0316538 A1 | 12/2012 | Heiser et al. |
| 2013/0053795 A1 | 2/2013 | Coulthard et al. |
| 2013/0053806 A1 | 2/2013 | Guillo et al. |
| 2013/0165837 A1 | 6/2013 | Addison et al. |
| 2013/0211318 A1 | 8/2013 | Croizat et al. |
| 2013/0231623 A1 | 9/2013 | Richard |
| 2013/0303975 A1 | 11/2013 | Gvodas, Jr. |
| 2014/0081192 A1 | 3/2014 | Wenske et al. |
| 2014/0114268 A1 | 4/2014 | Auguste et al. |
| 2014/0155790 A1 | 6/2014 | Argenta et al. |
| 2014/0207027 A1 | 7/2014 | Navia et al. |
| 2014/0309574 A1 | 10/2014 | Cotton |
| 2015/0005678 A1 | 1/2015 | Wall |
| 2015/0088085 A1 | 3/2015 | Rovaniemi |
| 2015/0119832 A1 | 4/2015 | Locke |
| 2015/0216733 A1 | 8/2015 | Allen et al. |
| 2016/0000610 A1 | 1/2016 | Riesinger |
| 2016/0038626 A1 | 2/2016 | Locke et al. |
| 2016/0074232 A1 | 3/2016 | Vitaris et al. |
| 2016/0128894 A1 | 5/2016 | Horton et al. |
| 2016/0166781 A1 | 6/2016 | Sarangapani et al. |
| 2016/0256665 A1 | 9/2016 | Doshi et al. |
| 2016/0262944 A1 | 9/2016 | Shmuelovitch et al. |
| 2017/0007751 A1 | 1/2017 | Hartwell et al. |
| 2017/0119940 A1 | 5/2017 | Quisenberry |
| 2018/0050137 A1 * | 2/2018 | Ryu ................ A61M 1/73 |
| 2019/0030223 A1 | 1/2019 | Lin |
| 2019/0030224 A1 | 1/2019 | Lin |
| 2019/0030226 A1 | 1/2019 | Lin |
| 2019/0133830 A1 | 5/2019 | Bishop et al. |
| 2019/0151156 A1 | 5/2019 | Kieswetter et al. |

FOREIGN PATENT DOCUMENTS

| | | |
|---|---|---|
| CN | 101969902 B | 2/2013 |
| CN | 102985096 A | 3/2013 |
| CN | 104024498 A | 9/2014 |
| CN | 106659590 A | 5/2017 |
| EP | 0206646 A2 | 12/1986 |
| EP | 0940131 A2 | 9/1999 |
| EP | 1219311 A2 | 7/2002 |
| EP | 1018967 B1 | 8/2004 |
| EP | 1674898 A1 | 6/2006 |
| EP | 1901686 A2 | 3/2008 |
| EP | 2995324 A1 | 3/2016 |
| EP | 3156016 A1 | 4/2017 |
| EP | 3157484 B1 | 2/2020 |
| GB | 288220 A | 8/1928 |
| GB | 2265314 A | 9/1993 |
| GB | 2329127 B | 8/2000 |
| GB | 2351025 A | 12/2000 |
| GB | 2365350 B | 2/2002 |
| GB | 2496310 B | 10/2015 |
| WO | 9605873 A1 | 2/1996 |
| WO | 0059418 A1 | 10/2000 |
| WO | 0059424 A1 | 10/2000 |
| WO | 03049660 A1 | 6/2003 |
| WO | 2004060148 A2 | 7/2004 |
| WO | 2003092620 A3 | 12/2004 |
| WO | 2005009488 A2 | 2/2005 |
| WO | 2005046761 A1 | 5/2005 |

(56) References Cited

FOREIGN PATENT DOCUMENTS

| | | | |
|---|---|---|---|
| WO | 2006081403 A1 | 8/2006 |
| WO | 2009141820 A1 | 11/2009 |
| WO | 2011130246 A2 | 10/2011 |
| WO | 2013066694 A2 | 5/2013 |
| WO | 2013123005 A1 | 8/2013 |
| WO | 2015193257 A1 | 12/2015 |
| WO | 2019027806 A1 | 2/2019 |
| WO | 2019027807 A1 | 2/2019 |
| WO | 2019027808 A1 | 2/2019 |
| WO | 2019027809 A1 | 2/2019 |
| WO | 2019027810 A1 | 2/2019 |

OTHER PUBLICATIONS

Application Guide: Pico multisite with softport technology applied to the heel, PCPE-48-0717-UE, Smith & Nephew, Inc. 2017.
Avance® Clinician's Guidelines, Revision Feb. 2017, Molnlycke Health Care US, LLC, Norcross, GA 30092.
BASF: Superabsorbent Fabric Keeps Feet Dry in All Weathers; Luquafleece from BASF in the IQ-Text Ventilation Element Clams Up in Tight in Wet Conditions, Oct. 7, 2008 (Year: 2008).
Borgquist, O., R. Ingemansson, M Malmsjö, Effects of negative pressure wound therapy on regional blood flow, wound contraction and fluid removal—Examining low pressure levels, intermittent and variable therapy, 24th Annual Clinical Symposium on Advances in Skin & Wound Care, San Antonio, Texas, USA—Oct. 22-25, 2009.
Borgquist, Ola, et al. Wound Edge Microvascular Blood Flow during Negative-Pressure Woulnd Therapy: Examining the Effects of Pressures from −10 to −175 mmHg, PRSJournal, vol. 125, No. 2, 2010, 502-509.
Cardinal Health NPWT Pro Family, Cardinal Health, Waukegan, IL, 2015.
Cardinal Health SVED Clinician User Manual, Cardinal Health, Waukegan, IL, 2015.
Cardinal Health SVED Patient User Manual, Cardinal Health, Waukegan, IL, 2015.
Cardinal Health SVED, "Clinitial Quick Reference Guide", Cardinal Health, the Netherlands, 2015, 2 pages.
Chanden K. Sen, Wound healing essentials: Let there be oxygen, Wound Rep Reg (2009) 17 1-18.
Eriksson, et al., Wet wound healing: from laboratory to patients to gene therapy, The American Journal of Surgery 188 (Suppl to Jul. 2004) 36S-41S.
EZCare Negative Pressure Wound Therapy, V1STA Negative Pressure Wound Therapy, Negative Pressure Wound Therapy Clinical Guidelines, BS-0039-0808, Smith & Nephew.
Final Rejection, U.S. Appl. No. 15/663,708, filed Apr. 15, 2020, 20 pages.
Final Rejection, U.S. Appl. No. 15/663,709, filed Jun. 5, 2020.
Final Rejection, U.S. Appl. No. 15/663,710, filed Nov. 25, 2019.
Final Rejection, U.S. Appl. No. 15/663,713, filed Jan. 10, 2020, 9 pages.
Final Rejection, U.S. Appl. No. 15/663,714, filed Feb. 3, 2020, 15 pages.

Ghatak, Schlanger, Ganesh, Lambert, Gordillo, Martinsek, and Roy, A Wireless Electroceutical Dressing Lowers Cost of Negative Pressure Wound Therapy, Adv Wound Care (New Rochelle) 4(5): 302-311, May 2015.
International Search Report for International Application No. PCT/US2018/043953 dated Oct. 9, 2018.
International Search Report for International Application No. PCT/US2018/043955 dated Oct. 17, 2018.
International Search Report for International Application No. PCT/US2018/043957 dated Oct. 19, 2018.
International Search Report for International Application No. PCT/US2018/043959 dated Oct. 15, 2018.
International Search Report for International Application No. PCT/US2018/043962 dated Oct. 16, 2018.
ITI Brings Hospitals New Value Model For Wound Care, Innovative Therapies, Inc. Copyright 2013 PR Newswire.
Leionkiewicz, M. Pawlaczyz, et al. Age-dependent biomechanical properties of the skin. Postepy Dermatol Alergol. 2013;30(5):302-306 (2013).
Malsmjo, MD, et al., Negative pressure wound therapy using gauze or polyurethane open cell foam: similar effects on would edge microvascular blood flow, Lund University, 1 page.
Merriam, Webster, Definition of Rigid 2022.
Niederauer, Mark Q. et al. Continuous diffusion of oxygen improves diabetic foot ulcer healing when compared with a placebo control: a randomised, double-blind, multicentre study, J. Wound Care, N. American Supplement, vol. 27, No. 9, Sep. 2018.
Non Final Rejection, U.S. Appl. No. 15/663,710, dated Jul. 11, 2019.
Non-Final Office Action, U.S. Appl. No. 15/663,708, dated Nov. 7, 2019.
Non-Final Rejection, U.S. Appl. No. 15/663,708, dated Nov. 7, 2019, 31pages.
Non-Final Rejection, U.S. Appl. No. 15/663,709, dated Oct. 10, 2019.
Non-Final Rejection, U.S. Appl. No. 15/663,713, dated Jun. 28, 2019.
Non-Final Rejection, U.S. Appl. No. 15/663,714, dated Sep. 13, 2019.
Pawlacqyk, Mariola, et al. Age-dependent biomechanical properties of the skin, Postepy Dermatol Alergol 2013,30(5):302-306;302-306.
Prevena Incision Management System, Clinician Guide, 390061 Rev C, KCI Licensing Inc., 2009.
Prevena Incision Management System, Product Monograph, KCI Licensing Inc., 2010.
Prospera Negaitve Pressure Wound Therapy, Pro-I, Advancing the Art and Science of NPWT, Prospera, Ft. Worth, Tx, 2008. MR-125-04/08.
Renasys Negative Pressure Wound Therapy, Pico Single Use Negative Pressure Wound Therapy System, NPCE-48-0613-NAE, Smith & Nephew, Inc., 2013.
V.A.C. Ulta Quick Reference Guide, KCI Licensing Inc., 2013.
V.A.C.Ulta™ Negative Pressure Wound Therapy System, KCI Licensing Inc., Apr. 17, 2016.
Vinidex, PVC Properties, accessed from URL: https://www.vinidex.com.au/technical-resources/material-properties/pvc-properties (2022), pp. 19.

* cited by examiner

APPARATUS AND METHODS FOR PRESSURE MANAGEMENT WITHIN A WOUND CHAMBER

CROSS-REFERENCE TO RELATED APPLICATIONS

This application is a continuation-in-part of co-pending U.S. patent application Ser. No. 15/663,709 filed 29 Jul. 2017, and this application is a continuation-in-part of U.S. patent application Ser. No. 15/663,710 filed 29 Jul. 2017, both of which are hereby incorporated by reference in their entireties herein.

BACKGROUND OF THE INVENTION

Field

This invention relates to medical devices, and more particularly, to wound therapy apparatus and related methods of operation.

Related Art

Wounds afflict hundreds of millions of people globally. While wounds are often traumatic in origin, wounds may also develop due to underlying physiological conditions such as morbidity of the vascular system. Wound and wound bed, as used herein, includes a localized region of tissue that has been affected by hostile factors, resulting in, for example, cellular abnormality such as swelling, inflammation, degradation, infection, or cell death. The wound bed represents an unhealed wound. In contrast, a healed wound is a skin surface that was previously injured but the focal breach is now entirely sealed and covered by varying amounts of epidermis and scar tissue. FIG. 1 illustrates an exemplary wound bed including some reference anatomy. As illustrated in FIG. 1, the wound bed may include varying degrees of exposure of underlying layers and structures along with possible infections and tissue changes. The wound bed, as illustrated, includes a localized region of tissue that has lost skin and been affected by hostile factors resulting in cellular abnormalities such as swelling, inflammation, degradation, infection, or cell death. The wound bed may include varying degrees of exposure of layers and structures that underlie the skin surface, as illustrated, along with possible infection and tissue changes. The wound bed may lie within a wound boundary that extends around the affected region at the skin surface of the skin. Wound boundary, as used herein, refers to the perimeter of the wound bed at the skin surface of the skin. The wound bed may extend contiguously in depth within the dermis, and the wound bed may extend yet deeper, for example, into subcutaneous fat, and deeper structures. Thus, the wound bed may include undermined flaps, sinuses, tunnels, and fistulae and the surrounding affected tissues.

Current negative pressure wound therapy (NPWT) devices may include an NPWT interface device. The NPWT interface device may include a dressing, a thin flexible sheet of generally fluid impervious polymer that is adhesive coated on portions of a distal side, and a single tube for fluid communication with the dressing. The dressing, may be, for example, cotton gauze, or open-cell foam made from polyvinyl alcohol or polyurethane.

After the dressing is packed into the wound bed, the sheet is then centered over the dressing and wound bed and then secured sealingly adhesively to the skin around the wound bed using the adhesive coating thereby sealing the wound bed and dressing. Finally, an aperture is created in the sheet over the dressing, and a connector and evacuation tube is sealingly engaged with that aperture thus forming the NPWT interface device. Air within a region between the sheet and the wound bed is evacuated through the tube to produce a suction pressure $p_s$ within the region that is less than the ambient pressure $p_{amb}$. The wound bed and surrounding skin contracts as the pressure within the region is decreased by suction pressure $p_s$, which causes the surrounding ambient pressure $p_{amb}$ to compresses the sheet and dressing upon the wound bed. Exudate from the wound bed may be drawn through the dressing and evacuated through the tube.

However, current NPWT devices suffer from various disadvantages. For example, the suction pressure $p_s$ within the region is typically alternated between about −125 mm Hg and about −25 mm Hg in current NPWT therapy regimens. However, by analogy, this variation in suction pressure $p_s$ is almost as ineffective at removing exudate from the wound bed as removing the content of a bottle by sucking at the mouth of the bottle.

Furthermore, due to the variable distance between the wound bed (which may be located anywhere from head to toe of a patient) and the suction pump (which is often placed by a bedside or carried near a patient's waist if portable), the suction pump and the NPWT interface device are typically connected by a tube of long length to accommodate various relative placements. The likely redundancy of the tube may result in the tube forming a dependent loop that may collect some exudate at low points within the tube, much like an elbow in a drain collects liquid. Evaporation is accelerated in such NPWT interface devices that are repeatedly subjected to suction causing exudate within the tube to evaporate forming a clog that at least partially occludes the tube. Because suction pressure $p_s$ is sensed within the tube not directly within the region between the sheet and the wound bed, occlusion of the tube may result in a false indication that proper therapy is being delivered to the wound bed when, in fact, proper therapy is not being delivered to the wound bed. For example, a suction pressure $p_s$ of −125 mm Hg may be sensed within the tube proximal of the occlusion, when, in fact, the suction pressure $p_s$ is very low or even non-existent distal of the occlusion (e.g., in the region between the sheet and the wound bed).

In order to correct this erroneous sensing problem, certain NPWT interface devices have a tube that includes multiple peripheral lumens formed in the tube peripheral to a central lumen. Fluid is then withdrawn from the region between the sheet and the wound bed through the central lumen, and the peripheral lumens are used for sensing the pressure within the region between the sheet and the wound bed. Pressure in the central lumen is also sensed to detect discrepancies between pressure in the central lumen and pressure in the peripheral lumens. For example, if the suction pressure $p_s$ within the region between the sheet and the wound bed sensed through the central lumen is high and the suction pressure $p_s$ within the region between the sheet and the wound bed sensed using the peripheral lumens is low, it may then be inferred that an occlusion such as an exudate plug is likely present in the central lumen.

However, such NPWT devices with peripheral lumens also have significant shortcomings. For example, the peripheral lumens by virtue of being small in size and used only for pressure sensing without communication of fluid therethrough may be prone to occlusion such as clogging with exudate, especially given the proximity of the peripheral lumen to the central lumen through which exudate is communicated. Thus, the availability of the peripheral lumens as sensing channels may be unreliable. Furthermore, the peripheral lumens sense suction pressure proximate the central lumen, not at other points within the NPWT interface device. This proximity of the peripheral lumens to the central lumen has, for example, the functional effect of placing a thermostat right next to an airflow inlet vent in a room and hoping to have a selected temperature within the entire room. Accordingly, the peripheral lumens in combination with the central lumen may not provide an accurate indication of the pressure within the region between the sheet and the wound bed.

Accordingly, there is a need for improved apparatus as well as related methods that provide an accurate indication of the pressure within the region between the sheet and the wound bed as well as provide accurate indications of various operational conditions.

BRIEF SUMMARY OF THE INVENTION

These and other needs and disadvantages may be overcome by the apparatus and related methods of use disclosed herein. Additional improvements and advantages may be recognized by those of ordinary skill in the art upon study of the present disclosure.

A wound therapy apparatus disclosed herein includes a wound interface sealingly securable to a skin surface around a wound bed to form an enclosed space over the wound bed, an inflow port disposed about the wound interface to form a portion of an inflow fluid pathway that communicates an inflow fluid into the enclosed space, and an outflow port disposed about the wound interface to form a portion of an outflow fluid pathway that communicates an outflow fluid out of the enclosed space, in various aspects. The outflow port is in spaced relation with the inflow port to define a flow path within the enclosed space having a length equivalent to a characteristic length of the enclosed space, in various aspects. An inflow pressure sensor is in communication with the inflow fluid pathway to detect an inflow pressure $p_{in}$ of the inflow fluid, and an outflow pressure sensor is in communication with the outflow fluid pathway to detect an outflow pressure $p_{out}$ of the outflow fluid, in various aspects. The inflow pressure $p_{in}$ and the outflow pressure $p_{out}$ in combination are indicative of a pressure $p_a$ within the enclosed space, in various aspects. In various aspects, the inflow pressure $p_{in}$ of the inflow fluid, a time rate of change of the inflow pressure $$\frac{dp_{in}}{dt}$$

of the inflow fluid, the outflow pressure $p_{out}$ of the outflow fluid, and a time rate of change of the outflow pressure $$\frac{dp_{out}}{dt}$$

of the outflow fluid are measured to determine an operational condition of the wound therapy apparatus.

This summary is presented to provide a basic understanding of some aspects of the apparatus and related methods disclosed herein as a prelude to the detailed description that follows below. Accordingly, this summary is not intended to identify key elements of the apparatus and methods disclosed herein or to delineate the scope thereof.

Figure 1:
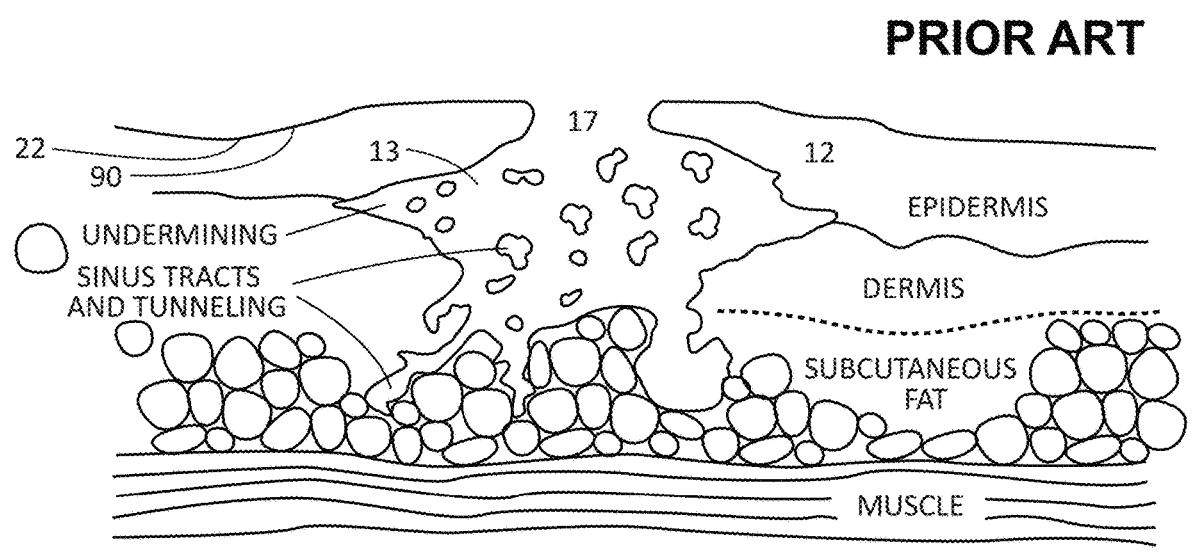
FIG. 1 illustrates an exemplary wound bed including various anatomical features thereof.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and other physical requirements are explained herein or are understandable to those of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations illustrated in the Figures and are utilized only to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

A wound therapy apparatus disclosed herein includes a wound interface sealingly securable to a skin surface around a wound bed to form an enclosed space over the wound bed, an inflow port disposed about the wound interface to form a portion of an inflow fluid pathway that communicates an inflow fluid into the enclosed space, and an outflow port disposed about the wound interface to form a portion of an outflow fluid pathway that communicates an outflow fluid out of the enclosed space, in various aspects. The outflow port is in spaced relation with the inflow port to define a flow path within the enclosed space having a length equivalent to a characteristic length of the enclosed space, in various aspects, so that a combination of an inflow pressure $p_{in}$ of the inflow fluid in the inflow fluid pathway and an outflow pressure $p_{out}$ are measured to measure a pressure $p_a$ within the enclosed space at the length equivalent to the characteristic length of the enclosed space. In various aspects, the inflow pressure $p_{in}$ of the inflow fluid, a time rate of change of the inflow pressure $$\frac{dp_{in}}{dt}$$

of the inflow fluid, the outflow pressure $p_{out}$ of the outflow fluid, and a time rate of change of the outflow pressure $$\frac{dp_{out}}{dt}$$

of the outflow fluid are measured to determine an operational condition of the wound therapy apparatus. Time rates of change of time rates of change $$\frac{d^2 p_{in}}{dt^2}, \frac{d^2 p_{out}}{dt^2}$$

(e.g., $2^{nd}$ derivatives) may be measured, in various aspects.

The pressure $p_a$ is the actual pressure within the enclosed space. The characteristic length defines a length scale of the enclosed space, and the characteristic length may be, for example, a diameter, a radius, a diagonal length, a side length, a hydraulic diameter, or a hydraulic radius. In various aspects, because the inflow port and the outflow port are spaced to define the flow path having length within the enclosed space commensurate with the characteristic length, the inflow pressure $p_{in}$ of the inflow fluid and outflow pressure pour of the outflow fluid are indicative of pressure $p_a$ within the enclosed space as measured at a length scale commensurate with the characteristic length of the enclosed space. That is, the length at which measurements of the pressure $p_a$ within the enclosed space is commensurate with the length scale of the enclosed space, in various aspects. For example, in aspects having a tube that communicates with the enclosed space, the characteristic length of the enclosed space and length of the flow path are both multiples of a diameter of the tube. Such aspects stand in contrast to pressure measurements of pressure $p_a$ within the enclosed space at a single location or at multiple locations separated by less than a diameter of the tube.

Fluid, as used herein, includes liquid(s), gas(ses), and combinations thereof. Liquid may include, for example, water, saline solution, proteolytic enzyme solutions, antimicrobial lavages, amniotic fluid, and exudate, and combinations thereof. Gas may include, for example, air, oxygen, nitric oxide, nitrogen, therapeutic or inert gasses, and combinations thereof. Exudate, as used herein, includes, for example, proteinaceous liquids exuded from the wound bed, along with various plasma and blood components. Exudate may also include other liquids used in treating the wound bed or produced by the wound bed or by surrounding tissues.

In various aspects, the term fluid-tight or related terms, as used herein, means sufficiently leak-resistant to allow insufflation or vacuum suction to create a pressure $p_a$ within the enclosed space that may be above or below ambient pressure $p_{amb}$. The term fluid-tight means sufficiently leak-resistant to substantially retain fluids including both gasses and liquids within the enclosed space other than by controlled fluid communication through one or more lumen that fluidly communicate through the wound interface with the enclosed space, in certain aspects. In certain aspects, fluid tight means sufficiently leak-resistant to maintain pressure $p_a$ within the enclosed space that may be above or below ambient pressure $p_{amb}$.

Ambient pressure $p_{amb}$, as used herein, refers to the pressure in a region surrounding the wound therapy apparatus. Ambient pressure $p_{amb}$, for example, may refer to atmospheric pressure, hull pressure within an aircraft or submarine where the wound therapy apparatus is being utilized, or pressure maintained generally within a building or other structure where the wound therapy apparatus is being utilized. Ambient pressure $p_{amb}$ may vary, for example, with elevation or weather conditions. Pressure $p_a$ within the enclosed space refers to the pressure actually occurring within the enclosed space. Minimum pressure $p_{min}$ refers to the minimum pressure achieved within the enclosed space of the wound therapy apparatus, and periodically varying of pressure $p_a$, pressure variation, varying pressure, and similar term refer to changes of pressure $p_a$ within the enclosed space over time. Maximum pressure $p_{max}$ refers to the maximum pressure achieved within the enclosed space of the wound therapy apparatus. Pressures such as suction pressure $p_s$, pressure $p_a$, minimum pressure $p_{min}$, and maximum pressure $p_{max}$ and their associated pressure values are as gauge pressure in this disclosure.

As used herein the terms distal and proximal are defined from the point of view of a physician, including various other healthcare providers, treating a patient with the wound therapy apparatus. When so treating the patient, a distal portion of the wound therapy apparatus is oriented toward the patient and a proximal portion of the wound therapy apparatus is oriented toward the physician. A distal portion of a structure is the portion closest to the patient while a proximal portion of the structure is the portion closet to the physician.

Although time rates of change such as $$\frac{dp_{out}}{dt} \text{ and } \frac{dp_{in}}{dt}$$

are expressed mathematically as differentials in this disclosure, it should be recognized that such time rates of change may be indicative of various approximations such as finite differences including other discretizations and approximations, and these approximations may be represented digitally in conformance to engineering, manufacturing, or scientific tolerances, as would be readily recognized by those of ordinary skill in the art upon study of this disclosure. For example, the finite difference representation of time rates of change such as $$\frac{dp_{out}}{dt} \text{ and } \frac{dp_{in}}{dt}$$

in various implementations may be limited by byte size and may include various errors such as roundoff error and truncation error. In various implementations, quantities such as suction pressure $p_s$, pressure $p_a$, inflow pressure $p_{in}$, outflow pressure $p_{out}$, minimum pressure $p_{min}$, and maximum pressure $p_{max}$ and time rates of change of pressure as used in the various mathematical relationships and formulations disclosed herein as well as the various mathematical relationships and formulations disclosed herein may include various errors such as roundoff error and truncation error and may conform to engineering, manufacturing, or scientific tolerances, as would be readily recognized by those of ordinary skill in the art upon study of this disclosure. Quantities such as suction pressure $p_s$, inflow pressure $p_{in}$, and outflow pressure $p_{out}$ as measured may be in the form of averages, median values, or other statistical representations of a plurality of measurements made using a sensor, in various implementations, and may include errors inherent in measurement by the sensor as well as errors in digital representations.

Figure 2:
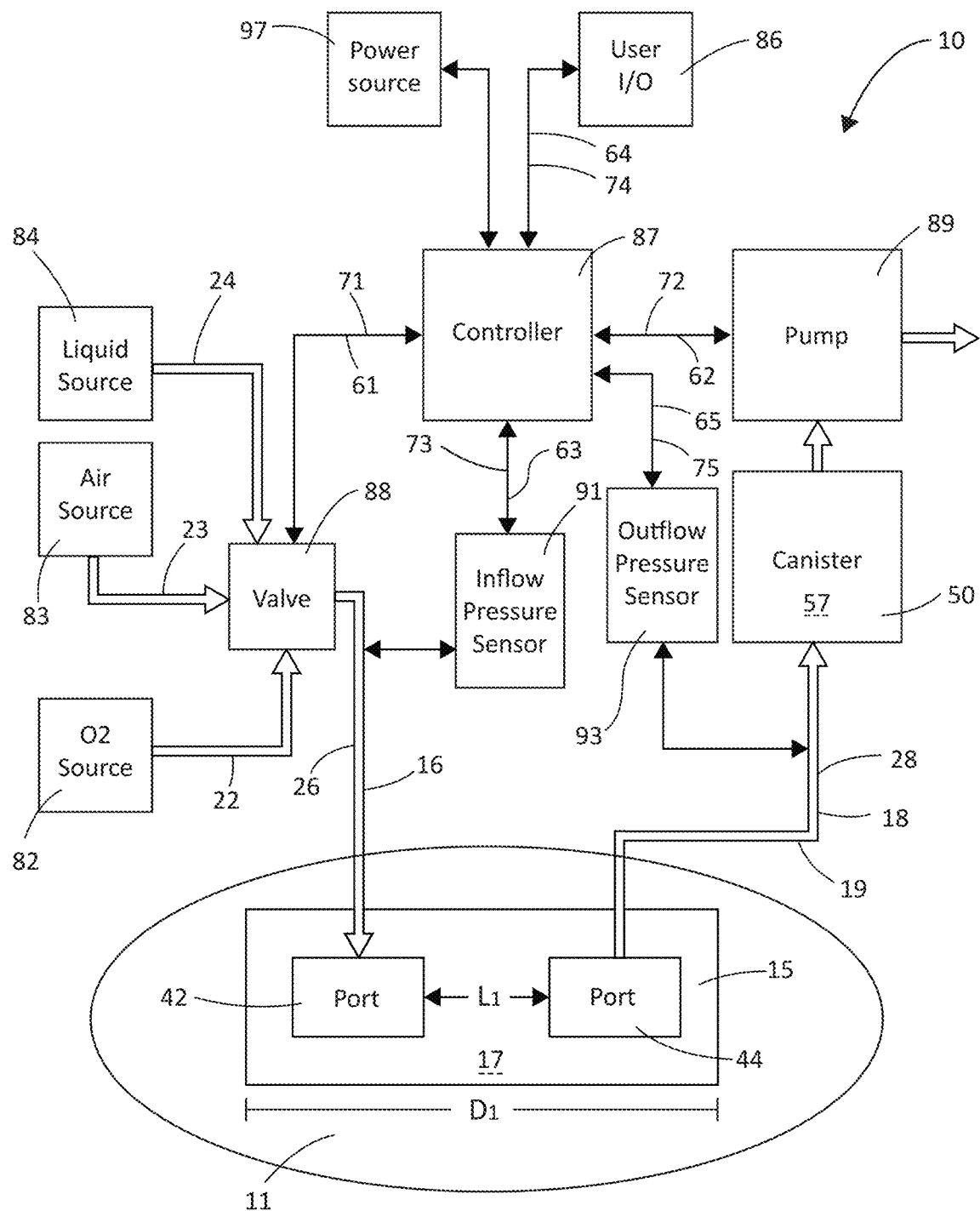
FIG. 2 illustrates by schematic diagram an exemplary implementation of a wound therapy apparatus.

FIG. 2 illustrates exemplary wound therapy apparatus 10. As illustrated in FIG. 2, wound interface 15 of wound therapy apparatus 10 is secured to skin surface 11 to define enclosed space 17 that is fluid tight over a wound bed (e.g., see FIG. 1; also wound bed 213 in FIG. 4E). In this implementation, wound therapy apparatus 10 includes oxygen source 82, air source 83, and liquid source 84 in fluid communication with enclosed space 17 of wound interface 15 via inflow fluid pathway 26 through inflow port 42 as controlled by valve 88. Inflow fluid pathway 26 includes inflow port 42. Valve 88, in turn, may be positioned by controller 87 to control the communication of oxygen 22 from oxygen source 82, air 23 from air source 83, liquid 24 from liquid source 84, or combinations of oxygen 22, air 23, and/or liquid 24 into enclosed space 17 as inflow fluid 16 via fluid pathway 26, as illustrated.

Pump 88 under control of controller 87 withdraws outflow fluid 18 from enclosed space 17 via fluid pathway 28, and outflow fluid pathway 28 includes outflow port 44. Outflow fluid 18 may include, for example, inflow fluid 16 and exudate 19, as illustrated. Liquid, such as liquid 24 and exudate 19, in outflow fluid 18 is captured in reservoir 57 of canister 50 as outflow fluid 18 is communicated through canister 50 by pump 89, and only gaseous portions of outflow fluid 18 are communicated from canister 50 to pump 89, in this implementation. Gaseous portions of outflow fluid 18 are discharged into the ambient environment by pump 89, as illustrated. Canister 50 including reservoir 57 may be omitted, for example, when the quantity of exudate 19 is minimal or there is no liquid, such as liquid 24 from liquid source 84, in outflow fluid 18. Canister 50 may be replaceable and disposable, in certain implementations.

Inflow pressure sensor 91 is in operable communication with inflow fluid pathway 26 to detect inflow pressure $p_{in}$ of inflow fluid 16 and the time rate of change of inflow pressure $$\frac{dp_{in}}{dt}.$$

Outflow pressure sensor 93 is in operable communication with outflow fluid pathway 28 to detect outflow pressure $p_{out}$ of outflow fluid 18 the time rate of change of outflow pressure $$\frac{dp_{out}}{dt}.$$

Inflow pressure sensor 91 may communicate with inflow fluid pathway 26 at one or more locations along inflow fluid pathway 26, for example, at or about oxygen source 82, air source 83, liquid source 84, valve 88, and/or within or about inflow port 42. Outflow pressure sensor 93 may communicate with outflow fluid pathway 28 at one or more locations along outflow fluid pathway, for example, within or about outflow port 44, reservoir 57 of canister 50, and/or suction side of pump 89.

Inflow port 42 and outflow port 44 are spaced length $L_1$ apart, and enclosed space 17 has characteristic length $D_1$, as illustrated. Characteristic length $D_1$ is a characteristic length of enclosed space 17 such as, for example, diameter, radius, diagonal length, side length, hydraulic diameter, hydraulic radius, and so forth, that defines a scale of enclosed space 17. Because inflow port 42 is located length $L_1$ from outflow port 44, inflow pressure $p_{in}$ detected by inflow pressure sensor 91 and outflow pressure $p_{out}$ detected by outflow pressure sensor 93 are indicative of pressure $p_a$ at locations length $L_1$ apart in enclosed space 17 proximate inflow port 42 and proximate outflow port 44, respectively. In various implementations, length $L_1$ may be commensurate with characteristic length $D_1$ of enclosed space 17, so that the inflow pressure $p_{in}$ detected by inflow pressure sensor 91 and outflow pressure $p_{out}$ detected by outflow pressure sensor 93 are commensurate with the scale of enclosed space 17. That is, in contrast to a single pressure measurement or multiple pressure measurements proximate one another, in exemplary wound therapy apparatus 10 pressure $p_a$ within enclosed space 17 is measured by measuring inflow pressure $p_{in}$ and outflow pressure $p_{out}$ at locations length $L_1$ apart where length $L_1$ is commensurate with characteristic length $D_1$ of enclosed space 17. In various implementations, length $L_1$ may be, for example, greater than 50% of characteristic length $D_1$. In various implementations, length $L_1$ may be, for example, greater than 80% of characteristic length $D_1$. In various implementations, length $L_1$ may be, for example, greater than 90% of characteristic length $D_1$.

Note that inflow pressure sensor 91 and outflow pressure sensor 93 are illustrated as separate pressure sensors for purposes of explanation. In various implementations, inflow pressure sensor 91 and outflow pressure sensor 93 may be formed as a single pressure sensor configured to detect inflow pressure $p_{in}$ and outflow pressure $p_{out}$, or inflow pressure sensor 91 or outflow pressure sensor 93 may be formed as multiple pressure sensors.

Controller 87 communicates operably with valve 88, pump 89, inflow pressure sensor 91, outflow pressure sensor 93, via communication pathway 61, 62, 63, 65, respectively, to control operations of valve 88, pump 89, inflow pressure sensor 91, and outflow pressure sensor 93 in order to deliver a therapy regimen within enclosed space 17. Controller 87 communicates operably with user I/O 86 to allow a user to control the operations of wound therapy apparatus 10, for example, to select the therapy regimen delivered within enclosed space 17. Controller 87 may control the operation of wound therapy apparatus 10, at least in part, based upon data 74 communicated to controller 87 from user I/O 86 via communication pathway 64, and controller 87 may control the operation of wound therapy apparatus 10, at least in part, based upon data 71, 72, 73, 75 communicated between controller 87 and valve 88, pump 89, inflow pressure sensor 91, and outflow pressure sensor 93 via communication pathways 61, 62, 63, 65, respectively.

Data 74 input from the user via user I/O 86 is communicated to controller 87, for example, in order to allow the user to direct the operation of wound therapy apparatus 10.

At least in part in response to data 74, controller 87 may direct delivery of various therapy regimens within enclosed space 17 of wound interface 15. For example, controller 87 may variously select inflow fluid 16 as oxygen 22 from oxygen source 82, air 23 from air source 83, liquid 24 from liquid source 84, or combinations thereof, and controller 87 may control the actual pressure $p_a$ within enclosed space 17 by controlling the inflow of inflow fluid 16 into enclosed space 17 and the withdrawal of outflow fluid 18 from enclosed space 17 through operations of valve 88 and pump 89. Controller 87 may alter the selection of inflow fluid 16 as oxygen 22 from oxygen source 82, air 23 from air source 83, liquid 24 from liquid source 84, combinations thereof, and/or the controller 87 may alter the pressure $p_a$ within enclosed space 17 over time according to the therapy regimen(s) being delivered. As examples, at certain times during the therapy regimen, (i) outflow fluid 18 is being withdrawn from enclosed space 17 while no inflow fluid 16 is being flowed into enclosed space 17 in order to reduce pressure $p_a$ to minimum pressure $p_{min}$; (ii) inflow fluid 16 is being flowed into enclosed space 17 while no outflow fluid 18 is being withdrawn from the enclosed space 17 in order to increase pressure $p_a$ to maximum pressure $p_{max}$; or, (iii) no inflow fluid 16 is being flowed into the enclosed space 17 and no outflow fluid 18 is being withdrawn from the enclosed space 17 as pressure $p_a$ is held at minimum pressure $p_{min}$ or at maximum pressure $p_{max}$.

Data 71 may be indicative of the operation of valve 88, for example, the position of valve 88—fully closed, fully open, intermediate of fully closed and fully open, allowing flow of oxygen 22 from oxygen source 82, allowing flow of air 23 from air source 83, allowing flow of liquid 23 from liquid source 84. Controller 87 may communicate data 71 with valve 88 to alter the operation of valve 88, for example, to select inflow fluid 16 as oxygen 22 from oxygen source 82, air 23 from air source 83, liquid 23 from liquid source 84, and combinations thereof. Controller 87 may communicate data 71 with valve 88 to alter the operation of valve 88, for example, to regulate, at least in part, the rate at which oxygen 22, air 23, liquid 24, or combinations thereof are flowed into enclosed space 17 as inflow fluid 16. It should be recognized that valve 88 is illustrated as a single valve 88 for purposes of explanation, and that, in various implementations, valve 88 may be formed as one or more valves of various types in various arrangements, as would be readily recognized by those of ordinary skill in the art upon study of this disclosure. For example, valve 88 may include one or more valves disposed about wound therapy apparatus to select inflow fluid 16 as gas 22, liquid 24, combinations of gas 22 and liquid 24, to regulate, at least in part, the inflow of inflow fluid 16 into enclosed space 17 of wound interface 15, and to regulate, at least in part, the withdrawal of outflow fluid 18 from enclosed space 17 of wound interface 15.

Data 72 communicated from pump 89 to controller 87 may be indicative of the operation of pump 89, for example, rate of operation, and quantity of electrical power being supplied. Pump 89 may be, for example, a centrifugal pump, positive displacement pump, or peristaltic pump, or multiple pumps of various types, in various implementations, and rate of operation refers to rate of rotation, rate of displacement, rate of contraction, etc. as appropriate. Data 72 communicated from controller 87 to pump 89 may alter the operation of pump 89, for example, setting pump 89 in an ON state, setting pump 89 in an OFF state, or controlling the rate of operation of pump 89 in order to control, at least in part, the withdrawal of outflow fluid 18 from enclosed space 17 including the rate at which outflow fluid 18 is withdrawn.

Data 73 indicative of the inflow pressure $p_{in}$ and/or the time rate of change of inflow pressure $$\frac{dp_{in}}{dt}$$

detected by inflow pressure sensor 91 is communicated with controller 87 via communication pathway 63, and data 75 indicative of the outflow pressure $p_{out}$ and/or the time rate of change of outflow pressure $$\frac{dp_{out}}{dt}$$

detected by outflow pressure sensor 93 is communicated with controller 87 via communication pathway 65, as illustrated. Controller 87 may communicate data 73 with inflow pressure sensor 91 to control the operation of inflow pressure sensor 91 such as, for example, the frequency at which inflow pressure $p_{in}$ is detected and locations along inflow fluid pathway 26 at which inflow pressure $p_{in}$ is detected. Controller 87 may communicate data 75 with outflow pressure sensor 93 to control the operation of outflow pressure sensor 93 such as, for example, the frequency at which outflow pressure $p_{out}$ is detected and locations along outflow fluid pathway 28 at which outflow pressure $p_{out}$ is detected. Controller 87 may control the operation of valve 88 in combination with the operation of pump 89 in order to achieve a specified pressure $p_a$ within enclosed space 17 as may be indicated by the inflow pressure $p_{in}$ detected by inflow pressure sensor 91 and outflow pressure $p_{out}$ detected by outflow pressure sensor 93.

Controller 87 may include, for example, a processor, memory, software operably communicating with the processor, A/D converter, D/A converter, clock, I/O connectors, and so forth, and controller 87 may be configured for example, as a single chip or as an array of chips disposed about a circuit board, as would be readily recognized by those of ordinary skill in the art upon study of this disclosure. In some implementations, controller 87 may be configured, at least in part, as software operatively received by a computer, and the computer may, for example, communicate by network with valve 88, pump 89, inflow pressure sensor 91, and outflow pressure sensor 93.

User I/O 86 may include various switches, push buttons, dials, sliders, graphs, and so forth, whether virtual or physical, for obtaining data 74 from the user. In certain implementations, user I/O 86 may be formed, at least in part, as software operably received by a computer. Controller 87 may communicate data 74 to user I/O 86 that may be indicative of the operation of wound therapy apparatus 10, and user I/O 86 may display data 74 to the user using physical display(s), virtual display(s), and combinations thereof.

Oxygen source 82 may be, for example, a cylinder of oxygen, an oxygen bag, an oxygen generator, or mains oxygen. Air source 83, may be, for example, ambient air at ambient pressure or compressed air such as a cylinder of air or mains air. Liquid source 84 may be, for example, a container of liquid or mains supply of liquid. Oxygen source 82, air source 83, and liquid source 84 may include various traps, filters, fittings, and so forth, as would be readily recognized by those of ordinary skill in the art upon study of this disclosure.

Inflow fluid 16 may be communicated under pressure of oxygen source 82 (e.g., a tank of compressed gas), pressure of air source 83, pressure of liquid source 84 (e.g., piezometric head at liquid source), with respect to pressure $p_a$ within enclosed space 17, suction of pump 89, and combinations thereof.

Wound therapy apparatus 10 may include various fluid conveyances, for example hoses, pipes, valves, tubing, connectors, pressure regulators, plenums, and various other fittings, that form inflow fluid pathway 26 for the communication of oxygen 22, air 23, and liquid 24 from gas source 82, air source 83, and liquid source 84, respectively, to enclosed space 17 of wound interface 15 as inflow fluid 16 and form outflow fluid pathway 28 for the communication of outflow fluid 18 withdrawn from enclosed space 17 of wound interface 15. Note that in various other implementations, at least one of inflow port 42 and outflow port 44 may be used for monitoring directly or indirectly parameters within the enclosed space such as pressure $p_a$, temperature, humidity, pH, tissue oxygenation level, blood flow, etc. to affect the therapy regimen delivered to the wound bed.

Communication pathways 61, 62, 63, 64, 65 may be, for example, wired, wireless, optical (e.g., fiberoptic, infrared), networked (e.g., Internet), or various combinations thereof, in various implementations. Valve 88, pump 89, inflow pressure sensor 91, and outflow pressure sensor 93 may include, for example, A/D converters, D/A converters, actuators, solenoids, stepper motors, microprocessors, to control the operations of valve 88, pump 89, inflow pressures sensor 91, and outflow pressure sensor 93 using data 71, 72, 73, 75 respectively, or to communicated data 71, 72, 73, 75 to controller 87 indicative of the operation of valve 88, pump 89, inflow pressure sensor 91, and outflow pressure sensor 93, as would be readily recognized by those of ordinary skill in the art upon study of the present disclosure. Data 71, 72, 73, 74, 75 may be digital, analog, or combinations thereof, in various implementations.

Power source 97 includes one or more source(s) of electrical power disposed about wound therapy apparatus 10 in electrical communication with wound therapy apparatus 10 including user I/O 86, controller 87, valve 88, pump 89, inflow pressure sensor 91, and outflow pressure sensor 93 to flow electrical power thereupon. Power source 97 may be, for example, mains electric, battery, or combinations of mains electric and battery, and power source 97 may include, for example, a transformer, an inverter, a rectifier, filter(s), surge protector(s), and so forth, as would be readily recognized by those of ordinary skill in the art upon study of the present disclosure. Wound therapy apparatus 10 may include various other fluid communication, data communication, electrical communication, and other pathways, as would be readily recognized by those of ordinary skill in the art upon study of this disclosure.

Figure 3A:
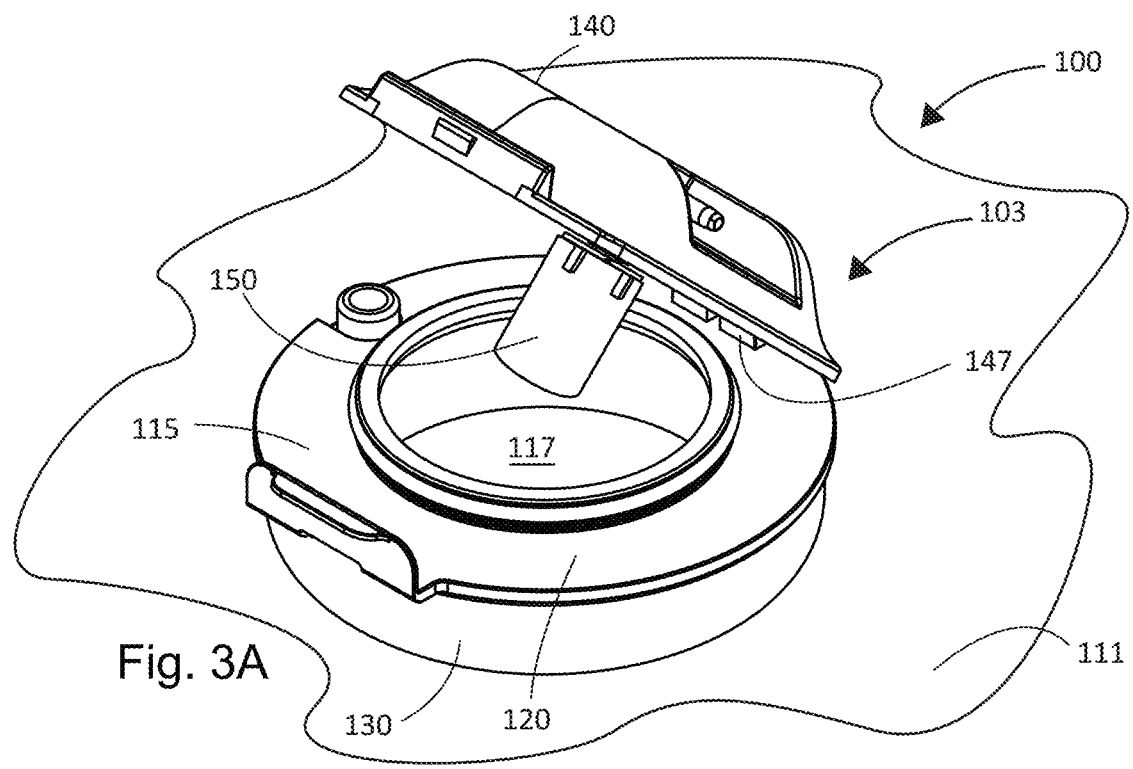
FIG. 3A illustrates by perspective view portions of a second exemplary implementation of a wound therapy apparatus in an open position.
Figure 3B:
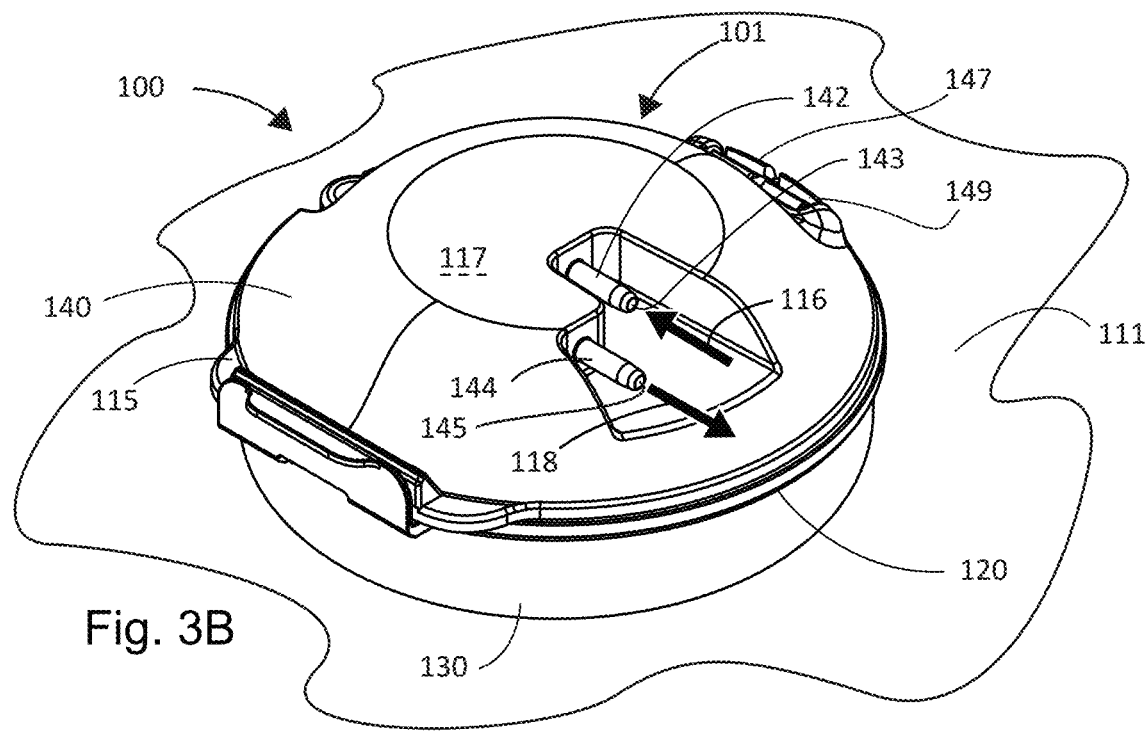
FIG. 3B illustrates by perspective view the second exemplary implementation of a wound therapy apparatus of FIG. 3A in a closed position.
Figure 3C:
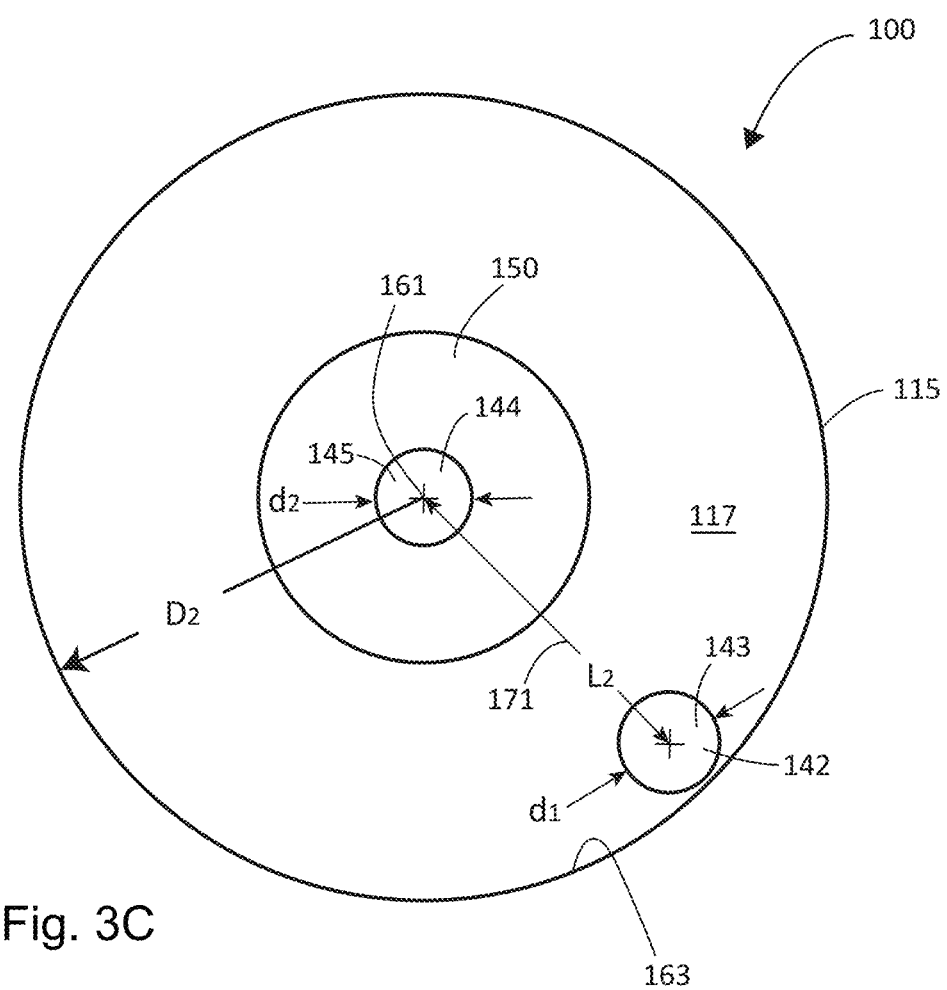
FIG. 3C illustrates by cross-sectional view portions of the second exemplary implementation of a wound therapy apparatus of FIG. 3A.

FIGS. 3A, 3B, 3C illustrate exemplary wound therapy apparatus 100. As illustrated in FIGS. 3A, 3B, exemplary wound therapy apparatus 100 includes wound interface 115, and wound interface 115 includes base 120, cushion 130, and cover 140, with cushion 130 secured circumferentially about the perimeter of base 120 to enclose the perimeter of base 120, and cover 140 secured hingedly to base 120 by hinge 147.

In various implementations, base 120 may be formed, for example, of one or more medical polymers including, for example, ABS, polystyrene or polypropylene, and base 120 may be structurally rigid. Cover 140 may be transparent, at least in part, to allow visual inspection of enclosed space 117 including a wound bed, such as wound bed 213 (see FIG. 4E; also see FIG. 1), and portions of skin surface 111 enclosed within enclosed space 117. Cover 140 may be formed, for example, from polycarbonate, acrylic, or similar clear polymer material such as copolyester available as Eastman Tritan™ from the Eastman Chemical Co.

As illustrated in FIGS. 3A, 3B, cushion 130 is annular shaped with footprint corresponding to that of a perimeter of base 120, as illustrated. Distal portions of cushion 130 may be secured sealingly adhesively around the entire perimeter to a skin surface, and proximal portions of cushion 130 are secured sealingly to base 120 around the entire perimeter of base 120. Cushion 130 cushions the wound interface 115 against the skin surface, and sealingly conforms to a contour of skin surface 111, in this implementation. In some implementations, cushion 130 may be formed, for example, of rubber or a polymer such as PVC or silicone, and cushion 130 may include an inner inflatable chamber. In such implementations, fluid, including air or other gasses or liquids within the inner inflatable chamber may be regulated to inflate cushion 130 to a desired level of cushioning and sealing of wound interface 115 with respect to the skin surface 111. In other implementations, cushion 130 may be formed, for example, of various compressible, conformable, fluid-impervious closed cell foams.

Cover 140 is hingedly attached to base 120 by hinge 147 that allows cover 140 to be positionable between open position 103, illustrated in FIG. 3A, and closed position 101, illustrated in FIG. 3B, to disengage or to engage sealingly, respectively, cover 140 with portions of base 120. Hinge 147 may be, for example, a living hinge, pinned hinge, snap-fit disengageable coupling, or other hinge, as would be readily understood by one of ordinary skill in the art upon study of this disclosure. Cover 140 may be engaged with base 120 by various other mechanisms such as a threaded engagement, or frictional engagement, in other implementations, that allow cover 140 to be sealingly engaged with base 120 and allow cover 140 to be disengaged from base 120. Cover 140 may be removably or non-removably engaged with base 120, in various implementations. Various seals, compression fittings, and so forth may be provided about cover 140, base 120, or cover 140 and base 120 to sealingly engage cover 140 with base 120 when cover 140 is positioned in closed position 101. Note that hinge 147 is optional, and may be omitted in certain implementations, for example, when no direct intervention to the wound bed is contemplated.

As illustrated in FIG. 3B, with cover 140 in closed position 101 and distal portions of cushion 130 secured circumferentially, sealingly, adhesively to skin surface 111, wound interface 115 defines enclosed space 117 that is fluid-tight. As illustrated in FIG. 3A, cover 140 may be positioned in open position 103 to conduct various direct interventions into enclosed space 117. Such direct interventions may include, for example, application of medicament to the wound bed and surrounding skin, debridement of necrotic tissue using medical maggots, and placement of a skin graft including other tissue graft onto the wound bed.

Base 120, as illustrated, has an annular shape, as illustrated in FIGS. 3A, 3B, 3C, to form a circular shaped enclosed space. It should be understood that wound interface 115, may assume other geometric shapes such as rectangular, polygonal, or ovoid, to enclose various shaped wounds or regions of skin surface 111, in various other implementations. The term "annular" as used in this disclosure is intended to describe these other geometric shapes, such as, for example, a polygonal, rectangular, or ovoid, base 120 surrounding enclosed space 117.

Inflow port 142 and outflow port 144 are disposed about cover 140, as illustrated, to fluidly communicate with enclosed space 117 when cover 140 is in closed position 101. As illustrated in FIG. 3C, inflow port 142 and outflow port 144 are spaced length $L_2$ apart, and enclosed space 117 has characteristic length $D_2$, which is a radius of enclosed space 117. Lumen 143 of inflow part 142 has diameter $d_1$ and lumen 145 of outflow port 144 has diameter $d_2$, as illustrated in FIG. 3C. Enclosed space 117 is circular in shape in this implementation, with inflow port 142 located proximate periphery 163 of enclosed space 117, and outflow port 144, located proximate center 161 of enclosed space 117. In other implementations, outflow port 144 may be located proximate periphery 163 and inflow port 142 may be located proximate center 161.

Fluid communication with inflow port 142 and with outflow port 144 may be at least in part via tubing (not shown) including hoses, pipes, valves, and various other fluid conveyances and fittings that may cooperate with inflow port 142 and outflow port 144, as would be readily recognized by those of ordinary skill in the art upon study of this disclosure.

Dressing 150, which is cylindrical in shape, extends forth from cover 140 to contact the wound bed when cover is in closed position 101, in this implementation. Dressing 150 may be variously sized to occupy various portions of enclosed space 117, and dressing 150 may be a therapeutic or protective material configured to intermittently contact the wound bed. Dressing 150 may be formed, for example, of cotton, absorbent foam, or fabric, and dressing 150 absorbs exudate 119 while allowing the transmission of fluids therethrough, in this implementation.

Inflow port 142 is located proximate periphery 163 to introduce inflow fluid 116 into enclosed space 117 via lumen 143 of inflow port 142. Outflow port 144 is positioned at center 161 so that lumen 145 of outflow port 144 fluidly communicates with dressing 150 for withdrawal of outflow fluid 118 from enclosed space 117. Outflow fluid 118 may include exudate, such as exudate 19, withdrawn from dressing 150, as well as inflow fluid 116 and other liquids and gasses that may be present within enclosed space 117. Thus, inflow fluid 116 inflows into enclosed space 117 via lumen 143 of inflow port 142 at periphery 163 of enclosed space 117, and outflow fluid 118 withdrawn from enclosed space 117 via lumen 145 of outflow port 144 at center 161 of enclosed space 117, so that fluid flow is generally from periphery 163 to center 161 of enclosed space 117 along flow path 171 with length $L_2 \approx D_2$, in this implementation. Length $L_2$ of flow path 171 may be multiple times the diameter $d_1$ of lumen 143 of inflow part 142 and length $L_2$ of flow path 171 may be multiple times the diameter $d_2$ of lumen 145 of outflow port 144. For example, length $L_2$ of flow path 171 may be at least 10 times the diameter $d_1$ of lumen 143 of inflow part 142. Length $L_2$ of flow path 171 may be at least 100 times the diameter $d_1$ of lumen 143 of inflow part 142, in certain implementations. In various implementations, length $L_2$ of flow path 171 may be greater than 50% of characteristic length $D_2$. In various implementations, length $L_2$ of flow path 171 may be greater than 80% of characteristic length $D_2$. In various implementations, length $L_2$ of flow path 171 may be greater than 90% of characteristic length $D_2$.

Figure 4A:
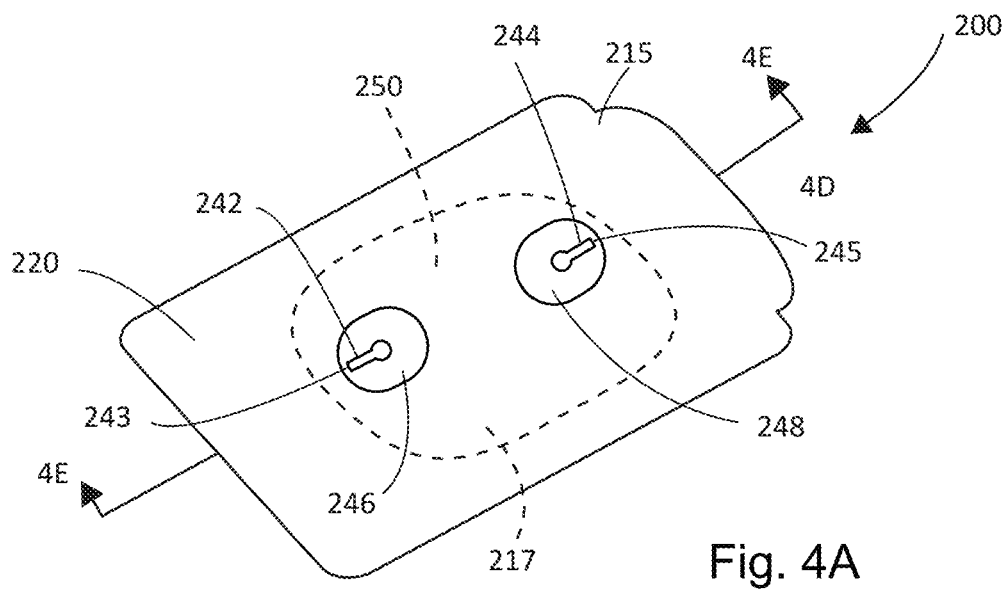
FIG. 4A illustrates by perspective view a third exemplary implementation of a wound therapy apparatus.
Figure 4B:
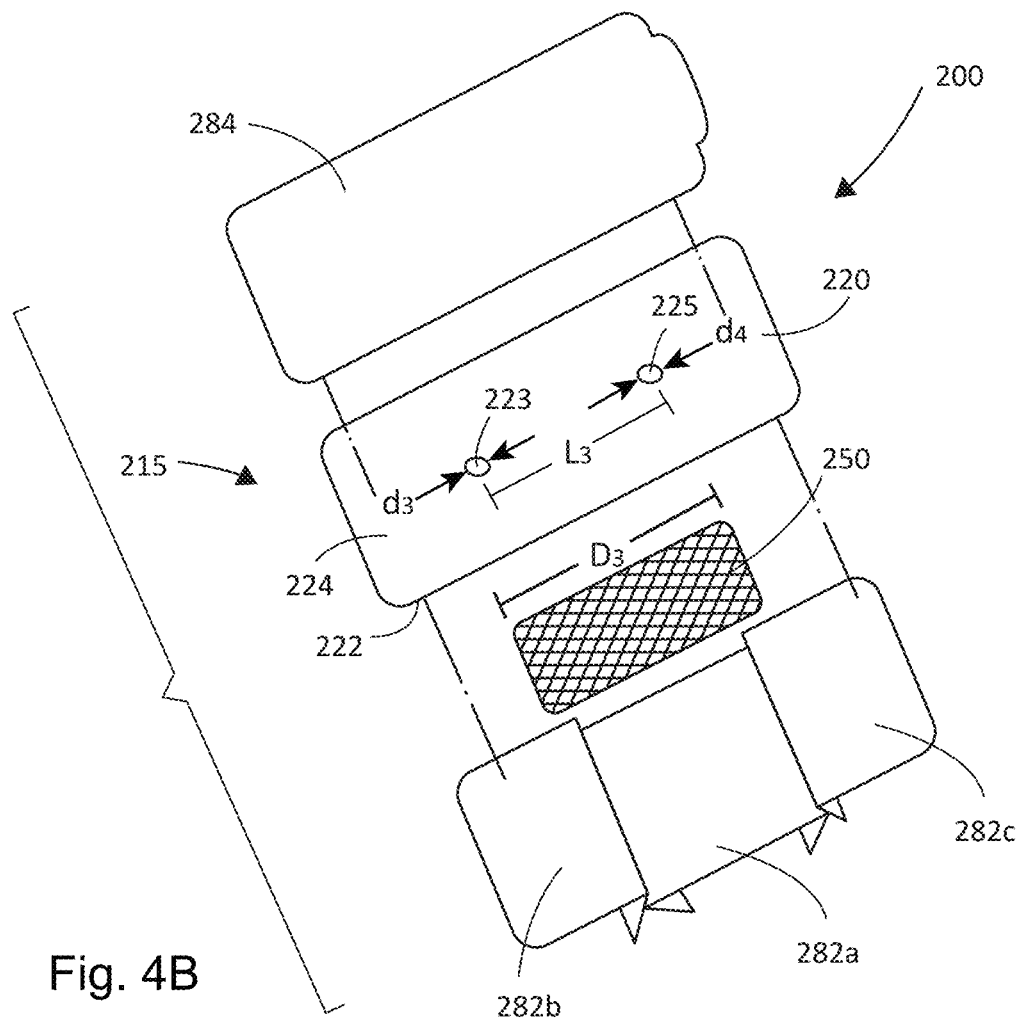
FIG. 4B illustrates by exploded view the third exemplary implementation of a wound therapy apparatus of FIG. 4A.
Figure 4C:
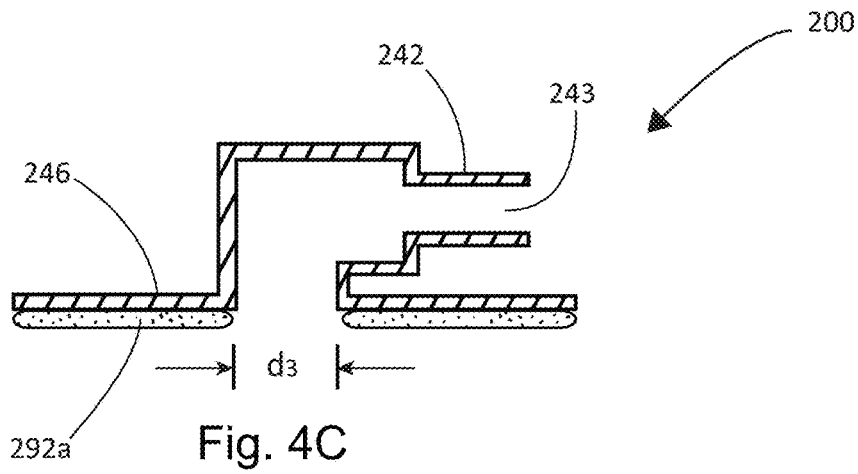
FIG. 4C illustrates by cut-away elevation views portions of the third exemplary implementation of a wound therapy apparatus of FIG. 4A.
Figure 4D:
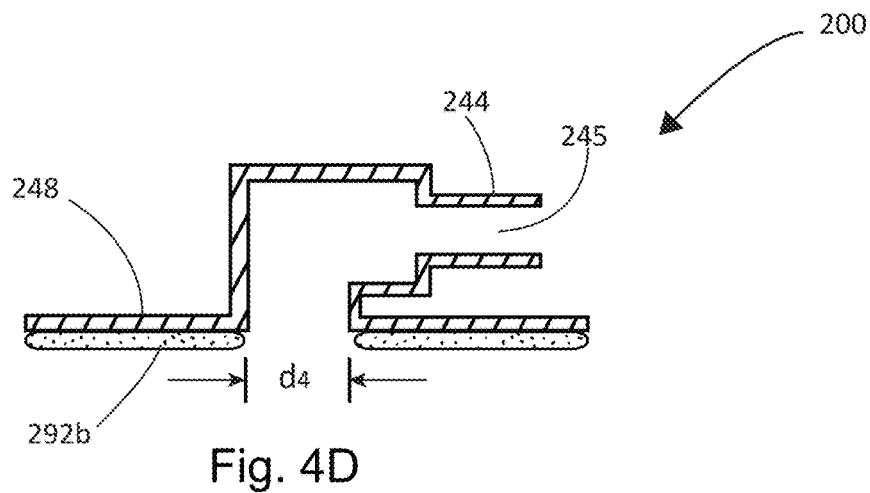
FIG. 4D illustrates by cut-away elevation views portions of the third exemplary implementation of a wound therapy apparatus of FIG. 4A.
Figure 4E:
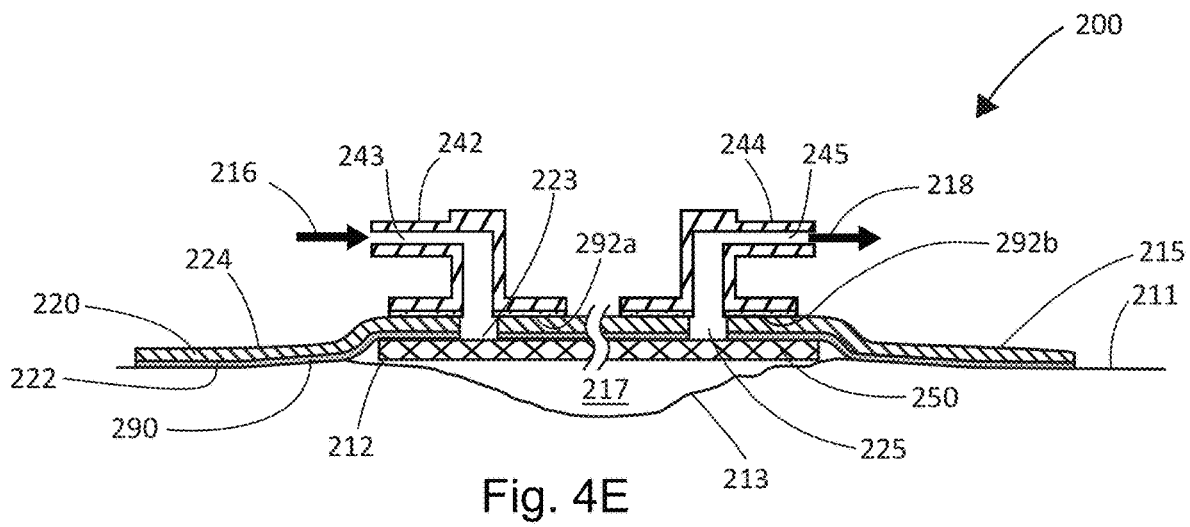
FIG. 4E illustrates by cut-away elevation view the third exemplary implementation of a wound therapy apparatus of FIG. 4A.

An exemplary implementation of a wound therapy apparatus 200 that includes wound interface 215 is illustrated in FIGS. 4A, 4B, 4C, 4D, 4E wherein wound interface 215 includes sheet 220, inflow port 242, outflow port 244, and dressing 250. Sheet 220 of wound interface 215 may be attached to skin surface 211 to enclose wound bed 213 at skin surface 211, with the entirety of wound boundary 212 enclosed by sheet 220, as illustrated in FIG. 4E. Distal side 222 of sheet 220 faces wound bed 213, and adhesive 290 on at least portions of distal side 222 secures sheet 220 to skin surface 211 thereby defining portions of enclosed space 217, as illustrated in FIG. 4E. Dressing 250 is packed into wound bed 213 and covered by sheet 220, as illustrated. Enclosed space 217 includes at least portions of wound bed 213, as illustrated. Sheet 220 may be made of a single layer of material such as polyurethane, in some implementations, or sheet 220 may be made of multiple layers of material, in other implementations.

As illustrated in FIG. 4E, inflow port 242 and outflow port 244 are in fluid communication with enclosed space 217 between distal side 222 of sheet 220 and proximal side 224 of sheet 220 through lumen 243, 245 formed within inflow port 242 and outflow port 244 and through apertures 223, 225 formed in sheet 220, respectively. Lumen 243, 245 have diameters $d_3, d_4$, respectively, as illustrated. Inflow fluid 216 may be flowed into enclosed space 217 via lumen 243 of inflow port 242 and outflow fluid 218 including exudate, such as exudate 19, may be withdrawn from enclosed space 217 via lumen 245 of outflow port 244.

Inflow of inflow fluid 216 into enclosed space 217 via lumen 243 of inflow port 242 and withdrawal of outflow fluid 218 from enclosed space 217 via lumen 245 of outflow port 244 may be sequential with one another, meaning inflow fluid 216 is not being inflowed into enclosed space 217 simultaneously with outflow fluid 218 being withdrawn from enclosed space 217. Inflow fluid 216 may be being inflowed into enclosed space 217 while no outflow fluid 218 is being withdrawn from enclosed space 217, outflow fluid 218 may be being withdrawn from enclosed space 217 while no inflow fluid 216 is being inflowed into enclosed space 217, or no inflow fluid 216 is being inflow into enclosed space 217 and no outflow fluid 218 is being withdrawn from enclosed space 217, in various implementations.

Inflow port 242 and outflow port 244 are spaced length $L_3$ apart to form flow path 271, and enclosed space 217 has characteristic length $D_3$, as illustrated. Inflow port 242 and outflow port 244 are located proximate opposing ends of enclosed space 217, in this implementation, to form flow path 271 of length $L_3$ where length $L_3$ is commensurate with characteristic length $D_3$ (e.g., $D_3 \approx L_3$). implementation. Length $L_3$ of flow path 271 may be multiple times the diameter $d_3$ of lumen 243 of inflow part 242 and length $L_3$ of flow path 271 may be multiple times the diameter $d_4$ of lumen 245 of outflow port 244. For example, length $L_3$ of flow path 271 may be at least 10 times the diameter $d_3$ of lumen 243 of inflow part 142. In various implementations, length $L_3$ of flow path 271 may be greater than 95% of characteristic length $D_3$ of enclosed space 217.

As illustrated in FIG. 4B, sheet 220 of wound therapy apparatus 200 may be supplied with carrier 284 in adhesive engagement with proximal side 224 of sheet 220 and liners 282a, 282b, 282c in adhesive engagement with distal side 222 of sheet 220. Carrier 284 may be made of paper or thin polymer sheet and carrier 284 is used to preserve the shape of sheet 220, which may be thin and prone to becoming entangled with itself. Liners 282a, 282b, 282c may be made of paper or thin polymer sheet and cover distal side 222 of sheet 220 including adhesive 290 until deployment of wound interface 215. For example, as wound interface 215 is deployed, dressing 250 is placed in wound bed 213. Then, liner 282a is peelingly removed from distal side 222 of sheet 220 to expose a portion of adhesive 290 on distal side 222.

The portion of adhesive 290 thus exposed is biased against skin surface 211 thereby anchoring sheet 220 to skin surface 211 by adhesive attachment. With sheet 220 anchored to skin surface 211, liners 282b, 282c are then removed and portions of adhesive 290 thus exposed are biased against skin surface 211 to attach distal side 222 of sheet 220 to skin surface 211. Sheet 220 covers dressing 250 and wound bed 213 and is adhesively attached to skin surface 211 around its perimeter in a fluid tight manner thus defining enclosed space 217. With sheet 220 attached to skin surface 211, carrier 284 is then removed from proximal side 224 of sheet 220. Inflow port 242 and outflow port 244 are then adhesively attached to proximal side 224 of sheet 220 using adhesive 292a, 292b on flanges 246, 248 illustrated in FIGS. 4C, 4D, respectively. When attached to proximal side 224 of sheet 220, inflow port 242 and outflow port 244 are placed with lumen 243, 245 aligned with apertures 223, 225 in sheet 220, respectively, to allow lumen 243, 245 to fluidly communicate with enclosed space 217 through apertures 223, 225 in sheet 220, as illustrated in FIG. 4E.

Figure 5:
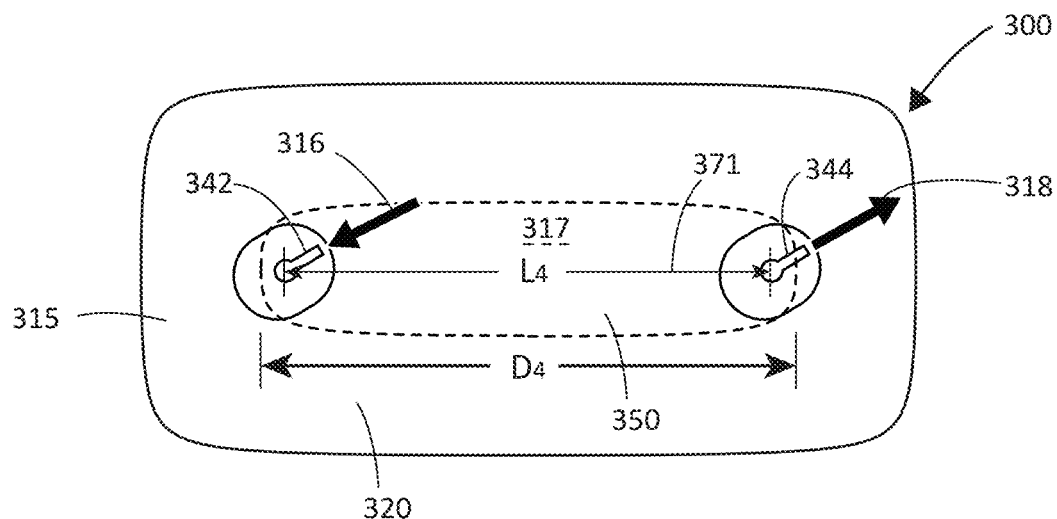
FIG. 5 illustrates by plan view portions of a fourth exemplary implementation of a wound therapy apparatus.

FIGS. 5, 6, 7, 8 illustrate exemplary wound therapy apparatus 300, 400, 500, 600, respectively. As illustrated in FIG. 5, wound therapy apparatus 300 includes wound interface 315, and wound interface 315 includes sheet 320 that overlays dressing 350 that has an elongated rectangular shape, and, thus, enclosed space 317 has an elongated rectangular shape of longitudinal characteristic length $D_4$. Inflow port 342 and outflow port 344 are set apart by length $L_4$ and located proximate ends of the elongated rectangular shape for form flow path 371 of length $L_4$ that fluid traverses between inflow port 342 and outflow port 344. Thus, inflow port 342 and outflow port 344 communicate fluidly with enclosed space 317 including dressing 350 proximate ends of the elongated rectangular shape so that length $L_4$ of flow path 371 is approximately equal to characteristic length $D_4$ (e.g., $D_4 \approx L_4$). Thus, inflow fluid 316 inflow into enclosed space 317 through inflow port 342 is communicated along flow path 371 that is the length of the elongated rectangular shaped enclosed space 317 for withdrawal as at least a portion of outflow fluid 318 through outflow port 344, in this implementation.

Figure 6:
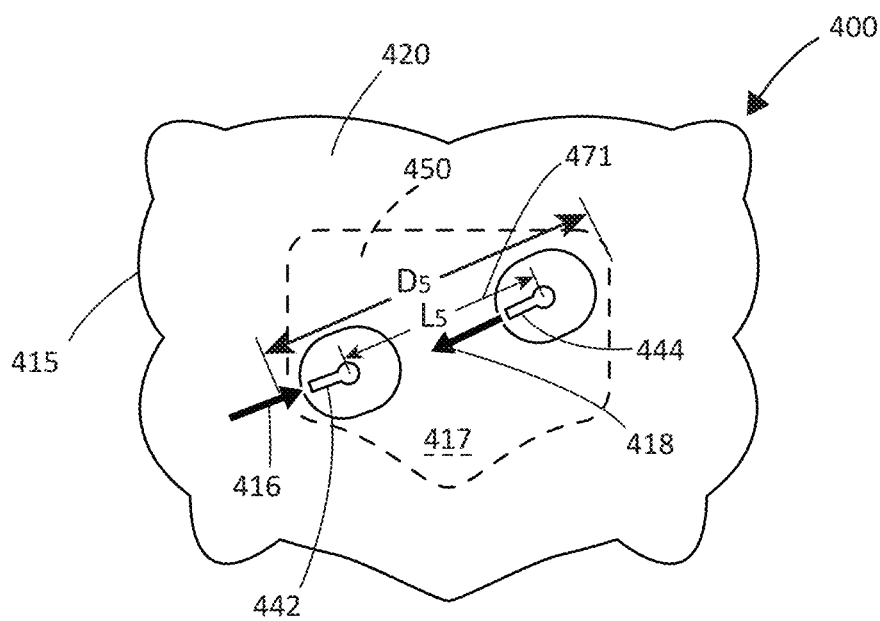
FIG. 6 illustrates by plan view portions of a fifth exemplary implementation of a wound therapy apparatus.

As illustrated in FIG. 6, wound therapy apparatus 400 includes wound interface 415 that has a square shape, and wound interface 415 includes sheet 420 that overlays dressing 450 shaped as an irregular pentagon (e.g., an isosceles right pentagon) in conformance to the shape of enclosed space 417. Enclosed space 417 has diagonal characteristic length $D_5$, in this implementation. Inflow port 442 and outflow port 444 are located proximate opposite corners of the irregular pentagonal enclosed space 417 set apart from one another by length $L_5$, as illustrated. Length $L_5$ is approximately equal to diagonal characteristic length $D_5$ (e.g., $D_5 \approx L_5$), in this implementation. Inflow fluid 416 inflow into enclosed space 417 through inflow port 442 is communicated along flow path 471 with length $L_5$ for withdrawal as at least a portion of outflow fluid 418 through outflow port 444, in this implementation. In implementations of wound therapy apparatus having an irregular polygonal shape, the characteristic length may be defined as a longest diagonal of the irregular polygonal shape.

Figure 7:
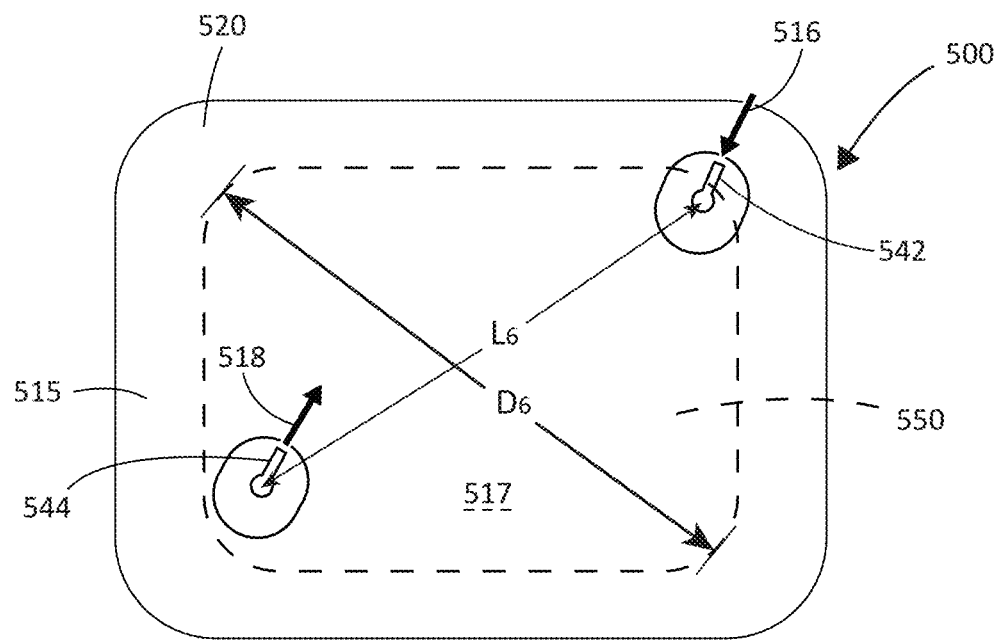
FIG. 7 illustrates by plan view portions of a sixth exemplary implementation of a wound therapy apparatus; and, FIG. 8 illustrates by plan view portions of a seventh exemplary implementation of a wound therapy apparatus.

As illustrated in FIG. 7, wound therapy apparatus 500 includes wound interface 515 that has a square shape, and wound interface 515 includes sheet 520 that overlays dressing 550 also of rectangular shape in conformance to the shape of sheet 520. Enclosed space 517 is thus rectangular in shape with diagonal characteristic length $D_6$, in this implementation. Inflow port 542 and outflow port 544 are located at opposite corners of the square shaped enclosed space 517 set apart from one another by length $L_6$. Length $L_6$ is approximately equal to diagonal characteristic length $D_6$ (e.g., $D_6 \approx L_6$), in this implementation. Thus, inflow fluid 516 is communicated into enclosed space 517 through inflow port 542 and is communicated along flow path 571 with length $L_6$ for withdrawal as at least a portion of outflow fluid 518 through outflow port 544, in this implementation.

Figure 8:
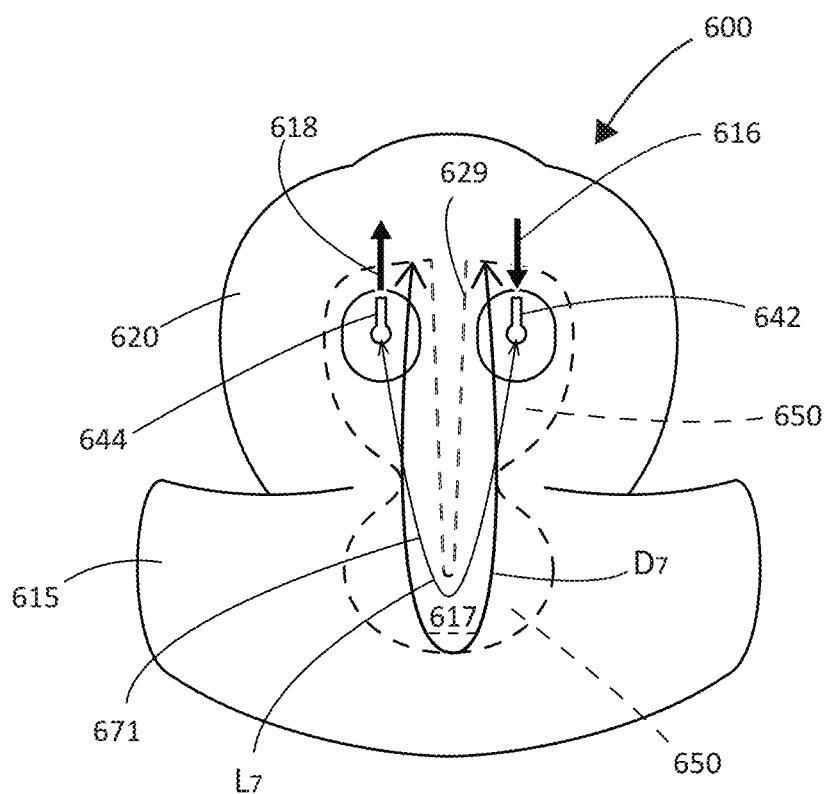

As illustrated in FIG. 8, wound therapy apparatus 600 includes wound interface 615, and wound interface 615 includes sheet 620 that overlays dressing 650. In this implementation, wound interface 615 is designed for application to a wound bed, such as wound bed 213 (also see FIG. 1), located about a heel (e.g., a decubitus ulcer of the heel), and is shaped accordingly. Enclosed space 617 includes U-shaped barrier 629, as illustrated, interposed between inflow port 642 and outflow port 644, to define enclosed space 617 having somewhat of an hourglass shape with mismatched hourglass chambers and characteristic length $D_7$. Inflow port 642 and outflow port 644 are located proximate one another on opposing sides of U-shaped barrier 629. Because of U-shaped barrier 629, inflow fluid 616 is communicated into enclosed space 617 through inflow port 642, along pathway 671 of length $L_7$ within enclosed space 617 for withdrawal as outflow fluid 618 through outflow port 644, in this implementation. Length $L_7$ is approximately equal to characteristic length $D_7$ (e.g., $D_7 \approx L_7$), in this implementation.

In operation of a wound therapy apparatus, such as wound therapy apparatus 10, 100, 200, 300, 400, 500, 600, a wound interface, such as wound interface 15, 115, 215, 315, 415, 515, 615 is attached to a skin surface, such as skin surface 11, 111, 211, to enclose a wound bed, such as wound bed 213 (also see FIG. 1), within an enclosed space, such as enclosed space 17, 117, 217, 317, 417, 517, 617. An inflow fluid pathway, such as inflow fluid pathway 26, is then placed in communication with the enclosed space through an inflow port, such as inflow port 42, 142, 242, 342, 442, 542, 642, and an outflow fluid pathway, such as outflow fluid pathway 28, is then placed in communication with the enclosed space through an outflow port, such as outflow port 44, 144, 244, 344, 444, 544, 644. Inflow fluid, such as inflow fluid 16, 116, 216, 316, 416, 516, 616, may then be communicated into the enclosed space via the inflow fluid pathway through the inflow port, and outflow fluid, such as outflow fluid 18, 118, 218, 318, 418, 518, 618, may be withdrawn from the enclosed space through the outflow port via the outflow fluid pathway in order to deliver a therapy regimen to the wound bed. Liquid, such as liquid 24 and exudate 19, entrained in the outflow fluid may be collected in a reservoir of a canister, such as reservoir 57 of canister 50. The therapy regimen may be selected by a user and communicated to a controller, such as controller 87, using a user I/O, such as user I/O 86.

As part of the therapy regimen, the inflow fluid may include oxygen from an oxygen source, such as oxygen 22 from oxygen source 82, air from an air source, such as air 23 from air source 83, liquid from a liquid source, such as liquid 24 from liquid source 84, or various combinations of oxygen, air, or liquid. The controller may select oxygen, air, liquid, or various combinations thereof as inflow fluid by positioning a valve, such as valve 88. The controller may regulate the inflow of inflow fluid into the enclosed space and withdrawal of outflow fluid from the enclosed space by regulating the valve and by regulating a pump, such as pump 87, in order to deliver the therapy regimen.

An inflow pressure sensor, such as inflow pressure sensor 91, is in operable communication with the inflow fluid pathway to detect inflow pressure $p_{in}$ of the inflow fluid and the time rate of change of inflow pressure $$\frac{dp_{in}}{dt}$$

of the inflow fluid in the inflow fluid pathway. An outflow pressure sensor, such as outflow pressure sensor 93, is in operable communication with the outflow fluid pathway to detect outflow pressure $p_{out}$ of the outflow fluid and the time rate of change of outflow pressure $$\frac{dp_{out}}{dt}$$

of the outflow fluid in the outflow fluid pathway. The controller may operate the valve and the pump and otherwise regulate the operation of the wound therapy apparatus using data, such as data 73, from the inflow pressure sensor and using data, such as data 75, from the outflow pressure sensor, where the data are indicative of inflow pressure $p_{in}$ of the inflow fluid, the time rate of change of inflow pressure $$\frac{dp_{in}}{dt}$$

of the inflow fluid, outflow pressure $p_{out}$ of the outflow fluid, and the time rate of change of outflow pressure $$\frac{dp_{out}}{dt}$$

of the outflow fluid.

Various operational conditions of wound therapy apparatus may be detected using the inflow pressure $p_{in}$ of the inflow fluid, the time rate of change of inflow pressure $$\frac{dp_{in}}{dt}$$

of the inflow fluid, outflow pressure $p_{out}$ of the outflow fluid, and the time rate of change of outflow pressure $$\frac{dp_{out}}{dt}$$

of the outflow fluid. Hysteresis of changes in the inflow pressure $p_{in}$, changes in the outflow pressure $p_{out}$, the time rate of change of inflow pressure $$\frac{dp_{in}}{dt},$$

the time rate of change of outflow pressure $$\frac{dp_{out}}{dt}$$

alone or in combination may be indicative of various operational conditions of the wound therapy apparatus including the wound bed.

In the following examples of exemplary operational conditions, it is considered that net fluid is being withdrawn from the enclosed space—the withdrawal of outflow fluid is greater than the inflow of inflow fluid so that pressure $p_a$ within the enclosed space is being decreased toward minimum pressure $p_{min}$. Examples of operational conditions, without limitation, include:

i) Normal Operation.

Inflow pressure $p_{in}$ of the inflow fluid in the inflow fluid pathway is generally equal to the outflow pressure $p_{out}$ of the outflow fluid and therefor indicative of pressure $p_a$ within the enclosed space. Mathematically, this may be stated as:

$$p_{in} \approx p_a \approx p_{out} \quad (1)$$

or $$|p_{in} - p_{out}| < \varepsilon \quad (2)$$

where $\varepsilon$ represents a sensitivity. The time rate of change of the inflow pressure $p_{in}$ generally tracks the time rate of change in outflow pressure $p_{out}$. That is:

$$\left\| \left| \frac{dp_{in}}{dt} \right| - \left| \frac{dp_{out}}{dt} \right| \right\| < \delta \quad (3)$$

where $\delta$ represents another sensitivity. Note that the brackets in the form of vertical lines (e.g., | |) denote absolute values of the quantities enclosed therein. Under normal operational conditions, the inflow pressure $p_{in}$ detected by the inflow pressure sensor and the outflow pressure $p_{out}$ detected by the outflow pressure sensor are indicative of pressure $p_a$ in the enclosed space proximate the inflow port and proximate the outflow port, respectively. The inflow port and the outflow port are separated by a length, such as length $L_1$, $L_2$, $L_3$, $L_4$, $L_5$, $L_6$, $L_7$, away from the outflow port, and the length may be commensurate with a characteristic length, such as characteristic length $D_1$, $D_2$, $D_3$, $D_4$, $D_5$, $D_6$, of the enclosed space, in various implementations. Inflow pressure $p_{in}$ and outflow pressure $p_{out}$ may, for example, be averaged to determine pressure $p_a$ in the enclosed space. Thus, pressure $p_a$ in the enclosed space is determined from inflow pressure $p_{in}$ and outflow pressure $p_{out}$ detected at the length apart with respect to the enclosed space.

ii) Occlusion of the Outflow Fluid Pathway.

The outflow pressure $p_{out}$ of the outflow fluid deviates from the inflow pressure $p_{in}$ of the inflow fluid by occlusion of the outflow fluid pathway between the enclosed space and the outflow pressure sensor. Because of the occlusion, the outflow pressure $p_{out}$ detected by the outflow pressure sensor is not indicative of pressure $p_a$ within the enclosed space and does not generally equal the inflow pressure $p_{in}$. Occlusion of the outflow fluid pathway may be caused, for example, by exudate, such as exudate 19, that accumulates and hardens within the outflow fluid pathway or liquid that collects at low points in the outflow fluid pathway. That is:

$$|p_{in} - p_{out}| > \varepsilon \quad (5)$$

and

-continued $$\left\lVert\frac{dp_{in}}{dt}\right\rvert - \left\lvert\frac{dp_{out}}{dt}\right\rvert\right\rVert > \delta \qquad (6)$$

Note that:

$$p_{in} \approx p_a \text{ but } p_{out} \neq p_a \qquad (7)$$

iii) Reservoir Filled.

The reservoir of the canister may become filled with liquid, in which case the time rate of change of outflow pressure $p_{out}$ of the outflow fluid increases due to resulting decreased volume within the outflow fluid pathway. Inflow pressure $p_{in}$ is generally equal to the outflow pressure $p_{out}$. That is:

$$|p_{in} - p_{out}| < \varepsilon \qquad (8)$$
and
$$\left\lvert\frac{dp_{out}}{dt}\right\rvert > \delta \qquad (9)$$

where $\delta$ is a sensitivity representing, at least in part, a maximum time rate of change outflow pressure $$\frac{dp_{out}}{dt}$$

at which the reservoir has capacity (i.e., is not filled).

iv) Leak in Sealing Engagement Between Wound Interface and Skin Surface.

Two bounding exemplary operational conditions are as follows. Note that operational conditions intermediate of these two bounding operational conditions may be possible. These bounding exemplary operational conditions are:

(1) If the leak is large including detachment of the wound interface from the skin surface, then the inflow pressure $p_{in}$ is generally equal to the outflow pressure $p_{out}$ and both are generally equal to ambient pressure $p_{amb}$. Because the inflow pressure $p_{in}$ and outflow pressure $p_{out}$ are generally unchanged, both $$\left\lvert\frac{dp_{in}}{dt}\right\rvert < \delta_1 \approx 0 \text{ and } \left\lvert\frac{dp_{out}}{dt}\right\rvert < \delta_2 \approx 0$$

where $\delta_1$ and $\delta_2$ are sensitivities. Accordingly, $p_{in} \approx p_a \approx p_{out} \approx p_{amb}$ so that $|p_{in} - p_{out}| < \varepsilon$.

(2) If the leak is small, then the time rate of change of inflow pressure $$\frac{dp_{in}}{dt}$$

lags the time rate of change of outflow pressure $$\frac{dp_{out}}{dt}$$

as net fluid is withdrawn from the enclosed space but inflow pressure $p_{in}$ and outflow pressure equilibrate $p_{out}$ after withdrawal of fluid is competed, which distinguishes this operational condition from occlusion of the outflow fluid pathway. That is:

$$\left\lVert\frac{dp_{out}}{dt}\right\rvert - \left\lvert\frac{dp_{in}}{dt}\right\rvert\right\rVert > \delta \qquad (10)$$
and
$$|p_{in} - p_{out}| < \varepsilon \qquad (11)$$

As used herein, sensitivity, such as sensitivity $\delta$, $\delta_1$, $\delta_2$, $\varepsilon$, accounts for roundoff error, truncation error, measurement error, provides damping or hysteresis, and so forth, as would be readily recognized by those of ordinary skill in the art upon study of this disclosure. In various implementations, the sensitivity may be a positive finite value that may approach zero as limited by the physical and digital numeric limitations of the wound therapy apparatus. In various implementations, the sensitivity may be experimentally derived, while, in theory, the sensitivity may approach zero.

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. The Abstract is not intended to identify key elements of the apparatus and methods disclosed herein or to delineate the scope thereof. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. A wound therapy apparatus, comprising:
 a wound interface sealingly securable to a skin surface around a wound bed to form an enclosed space over the wound bed;
 an inflow port disposed about the wound interface to form a portion of an inflow fluid pathway that communicates an inflow fluid into the enclosed space;
 an outflow port disposed about the wound interface to form a portion of an outflow fluid pathway that communicates an outflow fluid out of the enclosed space, the outflow port in spaced relation with the inflow port to define a flow path within the enclosed space equivalent to a characteristic length of the enclosed space;
 an inflow pressure sensor in communication with the inflow fluid pathway to detect an inflow pressure $p_{in}$ of the inflow fluid;
 an outflow pressure sensor in communication with the outflow fluid pathway to detect an outflow pressure $p_{out}$ of the outflow fluid; and
 wherein the inflow pressure $p_{in}$ and the outflow pressure $p_{out}$ in combination are indicative of a pressure $p_a$ within the enclosed space.

2. The apparatus of claim 1, wherein the enclosed space has a circular shape and the characteristic length is defined as a radius of the circular shape.

3. The apparatus of claim 1, wherein the enclosed space has a rectangular shape and the characteristic length is defined as a diagonal of the rectangular shape.

4. The apparatus of claim 1, wherein the wound interface has a square shape and the characteristic length is defined as a diagonal of the square shape.

5. The apparatus of claim 1, wherein the wound interface has an irregular polygonal shape and the characteristic length is defined as a longest diagonal of the irregular polygonal shape.

6. The apparatus of claim 1, wherein the wound interface has a U shape and the characteristic length is defined from end to end of the U shape.

7. The apparatus of claim 1, further comprising:
a controller in operative communication with the inflow pressure sensor and with the outflow pressure sensor to receive data from the inflow pressure sensor and from the outflow pressure sensor, the data indicative of the inflow pressure $p_{in}$ of the inflow fluid, a time rate of change of the inflow pressure $$\frac{dp_{in}}{dt},$$

the outflow pressure $p_{out}$ of the outflow fluid, and a time rate of change of the outflow pressure $$\frac{dp_{out}}{dt};$$

and
wherein the controller determines an operational condition of said wound therapy apparatus using the data.

8. The apparatus of claim 7, wherein the operational condition is indicated by $|p_{in}-p_{out}|<\varepsilon$ where $\varepsilon$ represents a sensitivity and $$\left\| \left|\frac{dp_{in}}{dt}\right| - \left|\frac{dp_{out}}{dt}\right| \right\| > \delta$$

where $\delta$ represents another sensitivity.

9. The apparatus of claim 7, wherein the operational condition is indicated by $|p_{in}-p_{out}|>\varepsilon$ where $\varepsilon$ represents a sensitivity and $$\left\| \left|\frac{dp_{in}}{dt}\right| - \left|\frac{dp_{out}}{dt}\right| \right\| > \delta$$

where $\delta$ represents another sensitivity.

10. The apparatus of claim 9, wherein a pulse of the input fluid is input into the enclosed space to clear an occlusion from the outflow fluid pathway upon indication of the operational condition.

11. The apparatus of claim 7, wherein the operational condition is indicated by $|p_{in}-p_{out}|<\varepsilon$ and by $$\left\| \left|\frac{dp_{out}}{dt}\right| - \left|\frac{dp_{in}}{dt}\right| \right\| > \delta$$

where $\varepsilon$ represents a sensitivity and $\delta$ represents another sensitivity.

12. The apparatus of claim 11, wherein the pressure $p_a$ within the enclosed space is decreased below ambient pressure $p_{amb}$ upon indication of the operational condition.

13. The apparatus of claim 7, wherein the operational condition is indicated by $$|p_{in} - p_{out}| < \varepsilon \text{ and by } \left|\frac{dp_{out}}{dt}\right| > \delta$$

where $\varepsilon$ represents a sensitivity and $\delta$ represents another sensitivity.

14. A wound therapy apparatus, comprising:
a wound interface sealingly securable to a skin surface around a wound bed to form an enclosed space over the wound bed;
an inflow fluid pathway that communicates the inflow fluid into the enclosed space;
an outflow fluid pathway that communicates an outflow fluid out of the enclosed space;
a sensor in communication with the inflow fluid pathway and in communication with the outflow fluid pathway to detect data indicative of the inflow pressure $p_{in}$ of the inflow fluid, a time rate of change of the inflow pressure $$\frac{dp_{in}}{dt},$$

the outflow pressure $p_{out}$ of the outflow fluid, and a time rate of change of the outflow pressure $$\frac{dp_{out}}{dt};$$

and
a processor in communication with the sensor to determine an operational condition of said wound therapy apparatus from the data.

15. The apparatus of claim 14, wherein the operational condition is indicated by $|p_{in}-p_{out}|<\varepsilon$ where $\varepsilon$ represents a sensitivity and $$\left\| \left|\frac{dp_{in}}{dt}\right| - \left|\frac{dp_{out}}{dt}\right| \right\| > \delta$$

where $\delta$ represents another sensitivity.

16. The apparatus of claim 14, wherein the operational condition is indicated by $|p_{in}-p_{out}|>\varepsilon$ where $\varepsilon$ represents a sensitivity and $$\left\| \left|\frac{dp_{in}}{dt}\right| - \left|\frac{dp_{out}}{dt}\right| \right\| > \delta$$

where $\delta$ represents another sensitivity.

17. The apparatus of claim 16, wherein a pulse of the input fluid is input into the enclosed space to clear an occlusion from the outflow fluid pathway upon indication of the operational condition.

18. The apparatus of claim 14, wherein the operational condition is indicated by $|p_{in}-p_{out}|<\varepsilon$ and by $$\left\| \left|\frac{dp_{out}}{dt}\right| - \left|\frac{dp_{in}}{dt}\right| \right\| > \delta$$

where ε represents a sensitivity and δ represents another sensitivity.

19. The apparatus of claim 18, wherein the pressure $p_a$ within the enclosed space is decreased below ambient pressure $p_{amb}$ upon indication of the operational condition.

20. The apparatus of claim 14, wherein the operational condition is indicated by $|p_{in}-p_{out}|<\varepsilon$ and by $$\left|\frac{dp_{out}}{dt}\right| > \delta$$

where ε represents a sensitivity and δ represents another sensitivity.

* * * * *